US 10,806,940 B2

(12) United States Patent
Kaib et al.

(10) Patent No.: US 10,806,940 B2
(45) Date of Patent: *Oct. 20, 2020

(54) SYSTEMS AND METHODS OF DELIVERING THERAPY USING AN AMBULATORY MEDICAL DEVICE

(71) Applicant: ZOLL MEDICAL CORPORATION, Chelmsford, MA (US)

(72) Inventors: Thomas E. Kaib, Irwin, PA (US); Marshal W. Linder, New Kensington, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 57 days.

This patent is subject to a terminal disclaimer.

(21) Appl. No.: 15/970,125

(22) Filed: May 3, 2018

(65) Prior Publication Data
US 2018/0296847 A1 Oct. 18, 2018

Related U.S. Application Data

(63) Continuation of application No. 15/408,965, filed on Jan. 18, 2017, now Pat. No. 9,987,497, which is a
(Continued)

(51) Int. Cl.
A61N 1/39 (2006.01)
A61N 1/372 (2006.01)
(Continued)

(52) U.S. Cl.
CPC ....... A61N 1/3931 (2013.01); A61N 1/37258 (2013.01); A61N 1/3987 (2013.01);
(Continued)

(58) Field of Classification Search
CPC ............... A61N 1/3931; A61N 1/3993; A61N 1/37258; A61N 1/3987; A61B 5/01;
(Continued)

(56) References Cited

U.S. PATENT DOCUMENTS 3,534,727 A 10/1970 Roman
3,553,651 A 1/1971 Bird et al.
(Continued)

FOREIGN PATENT DOCUMENTS

EP 1642616 A2 4/2006
EP 1455640 B1 1/2008
(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.
(Continued)

Primary Examiner — Rex R Holmes
(74) Attorney, Agent, or Firm — Lando & Anastasi, LLP

(57) ABSTRACT

An ambulatory medical device capable of delivering therapy to a patient includes at least one response mechanism having a state capable of being activated by one response button; a controller operatively connected with the at least one response mechanism, the controller including at least one processor coupled with a memory; and a therapy manager component executable by the controller and configured to detect a physiological parameter having a value indicative of a health disorder of the patient, notify the patient of impending therapy delivery in response to the detection of the physiological parameter, monitor the state of each at least one response mechanism within at least one predetermined time period, and delay therapy delivery to the patient in response to detection of a change in the state in a single response mechanism of the at least one response mechanism within the at least one predetermined time period.

28 Claims, 9 Drawing Sheets

Related U.S. Application Data continuation of application No. 14/318,186, filed on Jun. 27, 2014, now Pat. No. 9,579,516.

(60) Provisional application No. 61/840,787, filed on Jun. 28, 2013.

(51) Int. Cl.

| | | |
|---|---|---|
| *A61B 5/01* | (2006.01) | |
| *A61B 5/0402* | (2006.01) | |
| *A61B 5/0408* | (2006.01) | |
| *A61B 5/08* | (2006.01) | |
| *A61B 5/00* | (2006.01) | |

(52) U.S. Cl.
CPC .............. *A61N 1/3993* (2013.01); *A61B 5/01* (2013.01); *A61B 5/0402* (2013.01); *A61B 5/04085* (2013.01); *A61B 5/04087* (2013.01); *A61B 5/0816* (2013.01); *A61B 5/6823* (2013.01)

(58) Field of Classification Search
CPC .............. A61B 5/04087; A61B 5/0402; A61B 5/04085; A61B 5/0816; A61B 5/6823
See application file for complete search history.

(56) References Cited

U.S. PATENT DOCUMENTS

| | | | |
|---|---|---|---|
| 4,094,310 | A | 6/1978 | McEachern et al. |
| 4,136,690 | A | 1/1979 | Anderson et al. |
| 4,422,459 | A | 12/1983 | Simson |
| 4,458,691 | A | 7/1984 | Netravali |
| 4,632,122 | A | 12/1986 | Johansson et al. |
| 4,928,690 | A | 5/1990 | Heilman et al. |
| 4,991,217 | A | 2/1991 | Garrett et al. |
| 5,000,189 | A | 3/1991 | Throne et al. |
| 5,062,834 | A | 11/1991 | Gross et al. |
| 5,078,134 | A | 1/1992 | Heilman et al. |
| 5,243,978 | A | 9/1993 | Duffin, Jr. |
| 5,330,505 | A | 7/1994 | Cohen |
| 5,342,404 | A | 8/1994 | Alt et al. |
| 5,348,008 | A | 9/1994 | Bornn et al. |
| 5,357,696 | A | 10/1994 | Gray et al. |
| 5,381,798 | A | 1/1995 | Burrows |
| 5,738,102 | A | 4/1998 | Lemelson |
| 5,741,306 | A | 4/1998 | Glegyak et al. |
| 5,758,443 | A | 6/1998 | Pedrazzini |
| 5,792,190 | A | 8/1998 | Olson et al. |
| 5,827,196 | A | 10/1998 | Yeo et al. |
| 5,887,978 | A | 3/1999 | Lunghofer et al. |
| 5,924,979 | A | 7/1999 | Swedlow et al. |
| 5,929,601 | A | 7/1999 | Kaib et al. |
| 5,944,669 | A | 8/1999 | Kaib |
| 6,016,445 | A | 1/2000 | Baura |
| 6,045,503 | A | 4/2000 | Grabner et al. |
| 6,047,203 | A | 4/2000 | Sackner et al. |
| 6,065,154 | A | 5/2000 | Hulings et al. |
| 6,097,987 | A | 8/2000 | Milani |
| 6,148,233 | A | 11/2000 | Owen et al. |
| 6,169,387 | B1 | 1/2001 | Kaib |
| 6,253,099 | B1 | 6/2001 | Oskin et al. |
| 6,280,461 | B1 | 8/2001 | Glegyak et al. |
| 6,406,426 | B1 | 6/2002 | Reuss et al. |
| 6,546,285 | B1 | 4/2003 | Owen et al. |
| 6,681,003 | B2 | 1/2004 | Linder et al. |
| 6,690,969 | B2 | 2/2004 | Bystrom et al. |
| 6,804,554 | B2 | 10/2004 | Ujhelyi et al. |
| 6,827,695 | B2 | 12/2004 | Palazzolo et al. |
| 6,865,413 | B2 | 3/2005 | Halperin et al. |
| 6,908,437 | B2 | 6/2005 | Bardy |
| 6,961,612 | B2 | 11/2005 | Elghazzawi et al. |
| 6,990,373 | B2 | 1/2006 | Jayne et al. |
| 7,074,199 | B2 | 7/2006 | Halperin et al. |
| 7,108,665 | B2 | 9/2006 | Halperin et al. |
| 7,118,542 | B2 | 10/2006 | Palazzolo et al. |
| 7,122,014 | B2 | 10/2006 | Palazzolo et al. |
| 7,149,579 | B1 | 12/2006 | Koh et al. |
| 7,220,235 | B2 | 5/2007 | Geheb et al. |
| 7,295,871 | B2 | 11/2007 | Halperin et al. |
| 7,340,296 | B2 | 3/2008 | Stahmann et al. |
| 7,453,354 | B2 | 11/2008 | Reiter et al. |
| 7,476,206 | B2 | 1/2009 | Palazzolo et al. |
| 7,488,293 | B2 | 2/2009 | Marcovecchio et al. |
| 7,712,373 | B2 | 5/2010 | Nagle et al. |
| 7,831,303 | B2 | 11/2010 | Rueter et al. |
| 7,974,689 | B2 | 7/2011 | Volpe et al. |
| 7,991,460 | B2 | 8/2011 | Fischell et al. |
| 8,121,683 | B2 | 2/2012 | Bucher et al. |
| 8,140,154 | B2 | 3/2012 | Donnelly et al. |
| 2003/0004547 | A1 | 1/2003 | Owen et al. |
| 2003/0023277 | A1 | 1/2003 | Owen et al. |
| 2003/0032988 | A1 | 2/2003 | Fincke |
| 2003/0095648 | A1 | 5/2003 | Kaib et al. |
| 2003/0109904 | A1 | 6/2003 | Silver et al. |
| 2003/0149462 | A1 | 8/2003 | White et al. |
| 2003/0158593 | A1 | 8/2003 | Heilman et al. |
| 2003/0174049 | A1 | 9/2003 | Beigel et al. |
| 2003/0195567 | A1 | 10/2003 | Jayne et al. |
| 2003/0212311 | A1 | 11/2003 | Nova et al. |
| 2004/0007970 | A1 | 1/2004 | Ma et al. |
| 2004/0049233 | A1 | 3/2004 | Edwards |
| 2004/0143297 | A1 | 7/2004 | Ramsey |
| 2004/0162510 | A1 | 8/2004 | Jayne et al. |
| 2004/0249419 | A1 | 12/2004 | Chapman et al. |
| 2005/0049515 | A1 | 3/2005 | Misczynski et al. |
| 2005/0131465 | A1 | 6/2005 | Freeman et al. |
| 2005/0144043 | A1 | 6/2005 | Holland et al. |
| 2005/0246199 | A1 | 11/2005 | Futch |
| 2005/0283198 | A1 | 12/2005 | Haubrich et al. |
| 2006/0036292 | A1 | 2/2006 | Smith et al. |
| 2006/0085049 | A1 | 4/2006 | Cory et al. |
| 2006/0095091 | A1 | 5/2006 | Drew |
| 2006/0178706 | A1 | 8/2006 | Lisogurski et al. |
| 2006/0211934 | A1 | 9/2006 | Hassonjee et al. |
| 2006/0220809 | A1 | 10/2006 | Stigall et al. |
| 2006/0264776 | A1 | 11/2006 | Stahmann et al. |
| 2006/0270952 | A1 | 11/2006 | Freeman et al. |
| 2007/0073120 | A1 | 3/2007 | Li et al. |
| 2007/0118056 | A1 | 5/2007 | Wang et al. |
| 2007/0129769 | A1 | 6/2007 | Bourget et al. |
| 2007/0143864 | A1 | 6/2007 | Cabana et al. |
| 2007/0161913 | A1 | 7/2007 | Farrell et al. |
| 2007/0169364 | A1 | 7/2007 | Townsend et al. |
| 2007/0196320 | A1 | 8/2007 | Yasin |
| 2007/0197878 | A1 | 8/2007 | Shklarski |
| 2007/0239214 | A1 | 10/2007 | Cinbis |
| 2007/0239220 | A1 | 10/2007 | Greenhut et al. |
| 2007/0265671 | A1 | 11/2007 | Roberts et al. |
| 2008/0021532 | A1 | 1/2008 | Kveen et al. |
| 2008/0030656 | A1 | 2/2008 | Watson et al. |
| 2008/0031270 | A1 | 2/2008 | Tran et al. |
| 2008/0033495 | A1 | 2/2008 | Kumar |
| 2008/0045815 | A1 | 2/2008 | Derchak et al. |
| 2008/0058884 | A1 | 3/2008 | Matos |
| 2008/0097793 | A1 | 4/2008 | Dicks et al. |
| 2008/0103402 | A1 | 5/2008 | Stickney et al. |
| 2008/0167535 | A1 | 7/2008 | Stivoric et al. |
| 2008/0177341 | A1 | 7/2008 | Bowers |
| 2008/0183090 | A1 | 7/2008 | Farringdon et al. |
| 2008/0249591 | A1 | 10/2008 | Gaw et al. |
| 2008/0287749 | A1 | 11/2008 | Reuter |
| 2008/0294019 | A1 | 11/2008 | Tran |
| 2008/0306560 | A1* | 12/2008 | Macho .................. A61B 5/0402 607/5 |
| 2008/0306562 | A1 | 12/2008 | Donnelly et al. |
| 2008/0312520 | A1 | 12/2008 | Rowlandson et al. |
| 2008/0312522 | A1 | 12/2008 | Rowlandson et al. |
| 2009/0018428 | A1 | 1/2009 | Dias et al. |
| 2009/0066366 | A1 | 3/2009 | Solomon |
| 2009/0073991 | A1 | 3/2009 | Landrum et al. |
| 2009/0076336 | A1 | 3/2009 | Mazar et al. |
| 2009/0076340 | A1 | 3/2009 | Libbus et al. |
| 2009/0076341 | A1 | 3/2009 | James et al. |

(56) References Cited

U.S. PATENT DOCUMENTS

| | | |
|---|---|---|
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076559 A1 | 3/2009 | Libbus et al. |
| 2009/0093687 A1 | 4/2009 | Telfort et al. |
| 2009/0118808 A1 | 5/2009 | Belacazar et al. |
| 2009/0138059 A1 | 5/2009 | Ouwerkerk |
| 2009/0146822 A1 | 6/2009 | Soliman |
| 2009/0212984 A1 | 8/2009 | Baker |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0114243 A1 | 5/2010 | Nowak et al. |
| 2010/0171611 A1 | 7/2010 | Gao et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0297594 A1 | 11/2010 | Sullivan et al. |
| 2010/0298899 A1 | 11/2010 | Donnelly et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0053479 A1 | 3/2012 | Hopenfeld |
| 2012/0158075 A1 | 6/2012 | Kaib et al. |
| 2012/0232355 A1 | 9/2012 | Freeman |
| 2013/0144355 A1 | 6/2013 | Macho et al. |
| 2013/0231711 A1* | 9/2013 | Kaib .................. G06F 19/3418 607/5 |

FOREIGN PATENT DOCUMENTS

| | | |
|---|---|---|
| EP | 1720446 B1 | 7/2010 |
| JP | 2002514107 | 9/1998 |
| JP | 2002-514107 A | 5/2002 |
| JP | 2002200059 A | 7/2002 |
| JP | 2008302225 | 12/2008 |
| JP | 2008302228 | 12/2008 |
| JP | 2009-521865 A | 6/2009 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |
| WO | 20120078857 | 6/2012 |

OTHER PUBLICATIONS

DeBock et al., "Captopril treatment of chronic heart failure in the very old," J. Gerontol. (1994) 49: M148-M152.

Extended European Search Report from corresponding EP Application No. 14817133.3 dated Mar. 2, 2017.

International Search Report from corresponding PCT application PCT/US2014/044660, dated Nov. 3, 2014.

O'Keeffe et al., "Reproducability and responsiveness of quality of the assessment and six minute walk test in elderly heart failure patients," Heart (1998) 80: 377-382.

Notice of Reasons for Refusal for Japanese Patent Application No. 2019-005891, dated Jan. 28, 2020, 5 pages.

* cited by examiner

SYSTEMS AND METHODS OF DELIVERING THERAPY USING AN AMBULATORY MEDICAL DEVICE

CROSS REFERENCE TO RELATED APPLICATIONS

This Application is a Continuation of U.S. patent application Ser. No. 15/408,965, titled "SYSTEMS AND METHODS OF DELIVERING THERAPY USING AN AMBULATORY MEDICAL DEVICE," filed on Jan. 18, 2017, now U.S. Pat. No. 9,987,497, which is a Continuation of U.S. patent application Ser. No. 14/318,186, titled "SYSTEMS AND METHODS OF DELIVERING THERAPY USING AN AMBULATORY MEDICAL DEVICE," filed on Jun. 27, 2014, now U.S. Pat. No. 9,579,516, which claims priority under 35 U.S.C. § 119(e) to U.S. Provisional Application Ser. No. 61/840,787 titled "SYSTEMS AND METHODS OF DELIVERING THERAPY USING AN AMBULATORY MEDICAL DEVICE," filed Jun. 28, 2013, all of which applications are hereby incorporated herein by reference in their entirety.

BACKGROUND

Technical Field

Aspects of the present invention relate to medical devices, and more particularly to apparatus and processes of delivering therapy using an ambulatory medical device.

Discussion

Some ambulatory medical devices deliver therapy to patients. For instance, an ambulatory medical device may monitor a patient's electrocardiogram (ECG) signal for indications of a cardiac abnormality. Where the ambulatory medical device identifies a cardiac abnormality that is treatable via the administration of a therapeutic shock, the ambulatory medical device may initiate a treatment protocol. When executing a treatment protocol, the ambulatory medical device must determine, with a high degree of accuracy, when it is appropriate to deliver therapy to the patient. The patient may, however, have the need to delay the administration of the therapy due to conditions that the ambulatory medical device is not configured to detect.

SUMMARY

In accordance with at least one aspect of the embodiments disclosed herein, an ambulatory medical device is provided. The ambulatory medical device accurately determines whether a patient requires a delay or prevention of the administration of therapy. In making this determination, the ambulatory medical device executes a process that is sensitive to and identifies potential false positives. For example, in some embodiments, the ambulatory medical device is configured to identify a state of responsiveness of the patient (e.g., a patient condition). Also, in some embodiments, the ambulatory medical device is configured to enable patients with poor dexterity or poor fine motor skills (including, but not limited to, patients with arthritis and diabetes) to engage a delay of treatment through one or more response mechanisms. The ambulatory medical device and the processes executed thereby may include audible and visual stimuli to a patient requesting the patient perform one or more specific actions within a predetermined amount of time to delay or prevent the administration of therapy.

According to an aspect, an ambulatory medical device capable of delivering therapy to a patient is provided. The ambulatory medical device comprises at least one sensor configured to detect a health disorder of the patient, at least one treatment element configured to deliver therapy to the patient, at least one response mechanism configured to be actuated by the patient, the at least one response mechanism having one of a first state and a second state, and at least one controller operatively connected to the at least one sensor, the at least one treatment element, and the at least one response mechanism. The at least one controller being configured to delay delivery of the therapy to patient for a first predetermined period of time responsive to detection of the health disorder and the at least one response mechanism having the first state, and to deliver the therapy to the patient in response to continued detection of the health disorder, the at least one response mechanism remaining in the first state, and a lack of responsiveness by the patient following expiration of the predetermined period of time.

According to an aspect, an ambulatory medical device capable of delivering therapy to a patient is provided. The ambulatory medical device comprises at least one response mechanism, the at least one response mechanism having a state that is one of a first state and a second state, a controller coupled with the at least one response mechanism, the controller including at least one processor coupled with a memory, and a therapy management component. The therapy management component being executable by the controller and configured to detect at least one physiological parameter having at least one value indicative of a health disorder of the patient, request the patient change the state of the at least one response mechanism from the first state to the second state in response to the detection of the at least one physiological parameter, monitor the state of the at least one response mechanism within a first predetermined period of time, delay administration of therapy to the patient in response to detection of a change in the state of the at least one response mechanism from the first state to the second state within the first predetermined period of time, monitor the state of the of the at least one response mechanism for a second predetermined period of time, request the patient change the state of the at least one response mechanism from the second state to the first state in response to detection of the state of the at least one response mechanism remaining in the second state for the second predetermined period of time, and one of further delay the administration of therapy in response to detection of a change in the state of the at least one response mechanism from the second state to the first state, and prepare to deliver the therapy to the patient in response to the state of the at least one response mechanism not changing from the second state to the first state following expiration of the second period of time.

According to an embodiment, the ambulatory medical device further comprises at least one therapy pad coupled with the controller, and at least one ECG sensor coupled with the controller. According to an embodiment, the ambulatory medical device is further configured to deliver at least one defibrillating shock to the patient via the at least one therapy pad and the therapy management component is configured to delay the administration of therapy to the patient by delaying the administration of the at least one defibrillating shock. According to an embodiment, the therapy management component is further configured to detect the at least one physiological parameter by monitoring a cardiac rhythm of the patient via the at least one ECG sensor. According to an embodiment, the therapy management component is further configured to detect the at least one physiological parameter having the at least one value indicative of the health disorder by detecting at least one physiological parameter having at least one value indicative of at least one of ventricular tachycardia, ventricular defibrillation, bradycardia, tachycardia, erratic heart rate, asystole, and pulseless electrical activity. According to an embodiment, the therapy management component is further configured to further delay the administration of therapy to the patient by further delaying the administration of therapy for a duration that is greater for ventricular tachycardia than for ventricular defibrillation.

According to an embodiment the ambulatory medical device includes a display coupled with the controller and the therapy management component is further configured to display, via the display, at least one notification requesting that the patient change the state of the at least one response mechanism. According to an embodiment, the therapy management component is further configured to display, via the display, one or more notifications to the patient indicating a delay in the administration of therapy to the patient.

According to an embodiment, the ambulatory medical device includes a speaker coupled with the controller and the therapy management component is further configured to request that the patient change the state in response to the detection of the at least one physiological parameter by generating audible alerts to the patient via the speaker. According to an embodiment, the therapy management component is further configured to generate, via the speaker, audible alerts to the patient indicating a delay in the administration of therapy to the patient.

According to an embodiment, the therapy management component is further configured to monitor a state of consciousness of the patient. According to an embodiment, the ambulatory medical device further includes an accelerometer coupled with the controller and the therapy management component is configured to monitor the state of consciousness of the patient by monitoring patient motion. According to an embodiment, the therapy management component is further configured to delay the administration of therapy in response to detection of targeted patient motion. According to an embodiment, the therapy management component is further configured to administer therapy to the patient in response to detection of a patient fall.

According to an embodiment, the ambulatory medical device includes a tactile stimulator coupled with the controller and the therapy management component is further configured to request the patient change the state of the at least one response mechanism by vibrating the ambulatory medical device controller via the tactile stimulator.

According to an embodiment, the therapy management component is configured to delay the administration of therapy to the patient in response to the detection of a change in the state of the at least one response mechanism from the second state to the first state within the second period of time by delaying the administration of therapy an interval of time selected based on a severity of the health disorder. According to an embodiment, the at least one response mechanism includes at least one response button. According to an embodiment, the first state of the at least one response button includes a deactivated state and the second state of the at least one response button includes an activated state.

According to an aspect, a method of delivering therapy to a patient using an ambulatory medical device is provided. The ambulatory medical device includes a controller coupled with at least one response mechanism, the at least one response mechanisms having a state that is one of a first state and a second state. The method comprises detecting, by the ambulatory medical device, at least one physiological parameter having at least one value indicative of a health disorder of the patient, requesting the patient change the at least one response mechanism from the first state to the second state in response to detecting the at least one physiological parameter, monitoring the state of at least one response mechanism within a first predetermined period of time, delaying administration of therapy to the patient in response to detecting a change in the state of the at least one response mechanism from the first state to the second state within the first predetermined period of time, monitoring the state of the at least one response mechanism for a second predetermined period of time, requesting the patient change the state of the at least one response mechanism from the second state to the first state in response to detecting the state of the at least one response mechanism remaining in the second state for the second predetermined period of time, and one of further delaying the administration of therapy in response to detection of a change in the state of the at least one response mechanism from the second state to the first state, and preparing to deliver the therapy to the patient in response to the state of the at least one response mechanism not changing from the second state to the first state following expiration of the second period of time.

According to an embodiment, the ambulatory medical device includes at least one electrocardiogram (ECG) sensor coupled with the controller and detecting, by the ambulatory medical device, the at least one physiological parameter includes detecting an ECG signal. According to an embodiment, the ambulatory medical device is configured to deliver at least one defibrillating shock to the patient via at least one therapy pad coupled with the controller and delaying the administration of therapy to the patient includes delaying the delivery of the at least one defibrillating shock. According to an embodiment, detecting, by the ambulatory medical device, the at least one physiological parameter includes monitoring a cardiac rhythm of the patient via the at least one ECG sensor. According to an embodiment, detecting, by the ambulatory medical device, the at least one physiological parameter having the at least one value indicative of the health disorder includes detecting at least one physiological parameter having at least one value indicative of at least one of ventricular tachycardia, ventricular defibrillation, bradycardia, tachycardia, erratic heart rate, asystole, and pulseless electrical activity.

According to an embodiment, the ambulatory medical device includes a display coupled with the controller and requesting that the patient change the state of the at least one response mechanism from the first state to the second state includes displaying at least one notification to the patient via the display. According to an embodiment, delaying the administration of therapy to the patient in response to detecting a change in the state of the at least one response mechanism from the first state to the second state includes displaying one or more notifications to the patient via the display.

According to an embodiment, the ambulatory medical device includes a speaker coupled with the controller and requesting that the patient change the state of the at least one response mechanism from the first state to the second state includes generating audible alerts to the patient via the speaker. According to an embodiment, delaying the administration of therapy to the patient in response to detecting a change from the first state to the second state includes generating audible alerts to the patient via the speaker.

According to an embodiment, the method further includes monitoring a state of consciousness of the patient. According to an embodiment, the method further includes delaying the administration of therapy to the patient in response to detecting a change in the state of the at least one response mechanism from the first state to the second state within the first predetermined period of time and a conscious patient in the second predetermined period of time. According to an embodiment, the ambulatory medical device further includes an accelerometer coupled with the controller and monitoring the state of consciousness of the patient includes monitoring patient motion. According to an embodiment, the method further includes administering therapy to the patient in response to detecting a patient fall.

According to an embodiment, the ambulatory medical device includes a tactile stimulator coupled with the controller and requesting that the patient change the state of the at least one response mechanism from the first state to the second state includes vibrating the ambulatory medical device controller via the tactile stimulator.

According to an embodiment, delaying further the administration of therapy to the patient in response to detecting a change in the state of the at least one response mechanism from the second state to the first state includes delaying the administration of therapy for a time interval selected based on a severity of the health disorder.

According to an aspect, a non-transitory computer readable medium storing executable instructions configured to instruct at least one controller to perform a method of delivering therapy is provided. The method comprises detecting, by the ambulatory medical device, at least one physiological parameter having at least one value indicative of a health disorder of the patient, requesting the patient change the at least one response mechanism from the first state to the second state in response to detecting the at least one physiological parameter, monitoring the state of at least one response mechanism within a first predetermined period of time, delaying administration of therapy to the patient in response to detecting a change in the state of the at least one response mechanism from the first state to the second state within the first predetermined period of time, monitoring the state of the at least one response mechanism for a second predetermined period of time, requesting the patient change the state of the at least one response mechanism from the second state to the first state in response to detecting the state of the at least one response mechanism remaining in the second state for the second predetermined period of time, and one of further delaying the administration of therapy in response to detection of a change in the state of the at least one response mechanism from the second state to the first state, and preparing to deliver the therapy to the patient in response to the state of the at least one response mechanism not changing from the second state to the first state following expiration of the second period of time.

According to an aspect, an ambulatory medical device capable of delivering therapy to the patient and configurable between a plurality of operation modes to delay administration of therapy is provided. The ambulatory medical device comprises two or more response mechanisms, each mechanism of the two or more response mechanisms having a status, a memory storing an active operation mode parameter identifying which of the plurality of operation modes is active, the plurality of operation modes including a first operation mode requiring changes in a status of one of the two or more response mechanisms, and the second operation mode requiring changes in a status of two of the two or more response mechanisms, a controller coupled with the two or more response mechanisms, the controller including at least one processor coupled with the memory, and a therapy management component. The therapy management component being executable by the controller and configured to identify the active operation mode from the plurality of operation modes, detect at least one physiological parameter having at least one value indicative of a health disorder of the patient, request that the patient change the status of one of the two or more response mechanisms in response to detection of the at least one physiological parameter and the identification of the first mode as the active operation mode, monitor the status of the two or more response mechanisms within a first predetermined period of time, and delay administration of therapy to the patient in response to detection of a first change in the status of one of the two or more response mechanisms within the first predetermined period of time and the identification of the first mode as the active operation mode.

According to an embodiment, the therapy management component is further configured to request, responsive to the detection the first change, that the patient change the status of one of the two or more response mechanisms, and monitor the status of the one or more response mechanisms within a second predetermined period of time, wherein the therapy management component is configured to delay the administration of therapy by delaying, responsive to the detection of the first change in the status within the first predetermined period of time and a second change in the status within the second predetermined period of time, the administration of therapy to the patient. According to an embodiment, the ambulatory medical device further comprises at least one therapy pad coupled with the controller, and at least one ECG sensor coupled with the controller. According to an embodiment, the ambulatory medical device is configured to deliver at least one defibrillating shock to the patient via the at least one therapy pad and the therapy management component is configured to delay in response to the detection of the first change in the status within the first predetermined period of time the administration of therapy to the patient by delaying the administration of the at least one defibrillating shock. According to an embodiment, the therapy management component is configured to detect the at least one physiological parameter by monitoring a cardiac rhythm of the patient via the at least one ECG sensor. According to an embodiment, the therapy management component is configured to detect the at least one physiological parameter having the at least one value indicative of the health disorder by detecting at least one physiological parameter having at least one value indicative of at least one of ventricular tachycardia, ventricular defibrillation, bradycardia, tachycardia, erratic heart rate, asystole, and pulseless electrical activity.

According to an embodiment, the therapy management component is configured to delay the administration of therapy to the patient by delaying the administration of therapy for a duration that is greater for ventricular tachycardia than for ventricular defibrillation. According to an embodiment, the ambulatory medical device includes a display coupled with the controller and the therapy management component is further configured to display, via the display, at least one notification requesting that the patient change the status. According to an embodiment, the therapy management component is further configured to display, via the display, one or more notifications to the patient indicating a delay in the administration of therapy to the patient. According to an embodiment, the ambulatory medical device includes a speaker coupled with the controller and the therapy management component is configured to request that the patient change the status in response to the detection of the at least one physiological parameter by generating audible alerts to the patient via the speaker. According to an embodiment, the therapy management component is further configured to generate, via the speaker, audible alerts to the patient indicating a delay in the administration of therapy to the patient.

According to an embodiment, the ambulatory medical device includes an accelerometer coupled with the controller and the therapy management component is configured to detect the at least one physiological parameter by detecting patient motion via the accelerometer. According to an embodiment, the therapy management component is further configured to increase the first predetermined period of time responsive to detection of targeted patient motion. According to an embodiment, the therapy management component is further configured to decrease the first predetermined period of time responsive to detection of a patient fall. According to an embodiment, the therapy management component is configured to delay the administration of therapy a first amount of time and wherein the therapy management component is further configured to delay the administration of therapy a second amount of time responsive to detecting targeted patient motion within the first predetermined period of time.

According to an embodiment, the ambulatory medical device includes a tactile stimulator coupled with the controller and the therapy management component is configured to request that the patient change the status in response to the detection of the at least one physiological parameter by vibrating the ambulatory medical device controller via the tactile stimulator. According to an embodiment, the therapy management component is configured to delay the administration of therapy to the patient in response to the detection of the first change in the status within the first predetermined period of time by delaying the administration for a time interval selected based on a severity of the health disorder. According to an embodiment, the therapy management component is configured to request that the patient change the status of at least two of the two or more response mechanisms in response to the detection of the at least one physiological parameter and the identification of the second mode as the operation mode.

According to an aspect, a method of delivering therapy to a patient using an ambulatory medical device is provided. The ambulatory medical device being configurable between a plurality of operation modes to delay administration of therapy, the ambulatory medical device including a controller coupled with two or more response mechanisms, each response mechanism of the two or more response mechanisms having a status. The method comprises identifying, by the ambulatory medical device, an active operation mode from the plurality of operation modes, the plurality of operation modes including a first operation mode requiring changes in a status of one of the two or more response mechanisms, and a second operation mode requiring changes in a status of two of the two or more response mechanisms, detecting, by the ambulatory medical device, at least one physiological parameter having at least one value indicative of a health disorder of the patient, requesting that the patient change the status of one of the two or more response mechanisms in response to detecting the at least one physiological parameter and identifying the first mode as the active operation mode, monitoring the status of the two or more response mechanisms within a first predetermined period of time, and delaying administration of therapy to the patient in response to detecting a first change in the status of one of the one or more response mechanisms within the first predetermined period of time and identifying the first mode as the active operation mode.

According to an embodiment, the method further includes requesting, responsive to detecting the first change, that the patient change the status of the one or more response mechanisms, and monitoring the status of the one or more response mechanisms within a second predetermined period of time, wherein delaying the administration of therapy to the patient includes delaying, responsive to detecting the first change in the status within the first predetermined period of time and a second change in the status within the second predetermined period of time, the administration of therapy to the patient.

According to an embodiment, the ambulatory medical device includes at least one electrocardiogram (ECG) sensor coupled with the controller and detecting, by the ambulatory medical device, the at least one physiological parameter includes detecting an ECG signal. According to an embodiment, the ambulatory medical device is configured to deliver at least one defibrillating shock to the patient via at least one therapy pad coupled with the controller and delaying the administration of therapy to the patient in response to detecting the first change within the first predetermined period of time includes delaying the delivery of the at least one defibrillating shock. According to an embodiment, detecting, by the ambulatory medical device, the at least one physiological parameter includes monitoring a cardiac rhythm of the patient via the at least one ECG sensor. According to an embodiment, detecting, by the ambulatory medical device, the at least one physiological parameter having the at least one value indicative of the health disorder includes detecting at least one physiological parameter having at least one value indicative of at least one of ventricular tachycardia, ventricular defibrillation, bradycardia, tachycardia, erratic heart rate, asystole, and pulseless electrical activity. According to an embodiment, the ambulatory medical device includes a display coupled with the controller and requesting that the patient change the status of at least one of the one or more response mechanisms in response to detecting the at least one physiological parameter includes displaying at least one notification to the patient via the display. According to an embodiment, delaying the administration of therapy to the patient in response to detecting the first change within the first predetermined period of time includes displaying one or more notifications to the patient via the display.

According to an embodiment, the ambulatory medical device includes a speaker coupled with the controller and requesting that the patient change the status in response to detecting the at least one physiological parameter includes generating audible alerts to the patient via the speaker. According to an embodiment, delaying the administration of therapy to the patient in response to detecting the first change within the first predetermined period of time includes generating audible alerts to the patient via the speaker. According to an embodiment, the ambulatory medical device includes an accelerometer coupled with the controller and detecting, by the ambulatory medical device, the at least one physiological parameter further includes detecting patient motion via the accelerometer. According to an embodiment, detecting the first change in the status within the first predetermined period of time includes increasing the first predetermined period of time responsive to detecting targeted patient motion. According to an embodiment, detecting the first change in the status within the first predetermined period of time includes decreasing the first predetermined period of time responsive to detecting a patient fall. According to an embodiment, delaying the administration of therapy includes delaying the administration of therapy a first amount of time and wherein the method further includes delaying the administration of therapy to the patient a second amount of time responsive to detecting targeted patient motion within the first predetermined period of time.

According to an embodiment, the ambulatory medical device includes a tactile stimulator coupled with the controller and requesting that the patient change the status in response to detecting the at least one physiological parameter includes vibrating the ambulatory medical device controller via the tactile stimulator. According to an embodiment, delaying, responsive to detecting the first change within the first predetermined period of time, the administration of therapy to the patient includes delaying the administration of therapy for a time interval selected based on a severity of the health disorder. According to an embodiment, the one or more response mechanisms include two or more response mechanisms and the method further includes requesting that the patient change the status of at least two of the two or more response mechanisms in response to detecting the at least one physiological parameter and identifying the second mode as the active operation mode.

According to an aspect, a non-transitory computer readable medium storing executable instructions configured to instruct at least one controller to perform a method of delivering therapy is provided. The method comprises identifying, by the ambulatory medical device, an active operation mode from the plurality of operation modes, the plurality of operation modes including a first operation mode requiring changes in a status of one of the two or more response mechanisms, and a second operation mode requiring changes in a status of two of the two or more response mechanisms, detecting, by the ambulatory medical device, at least one physiological parameter having at least one value indicative of a health disorder of the patient, requesting that the patient change the status of one of the two or more response mechanisms in response to detecting the at least one physiological parameter and identifying the first mode as the active operation mode, monitoring the status of the two or more response mechanisms within a first predetermined period of time, and delaying administration of therapy to the patient in response to detecting a first change in the status of one of the one or more response mechanisms within the first predetermined period of time and identifying the first mode as the active operation mode.

Still other aspects, embodiments, and advantages of these exemplary aspects and embodiments, are discussed in detail below. Moreover, it is to be understood that both the foregoing information and the following detailed description are merely illustrative examples of various aspects, and are intended to provide an overview or framework for understanding the nature and character of the claimed subject matter. Any embodiment disclosed herein may be combined with any other embodiment. References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
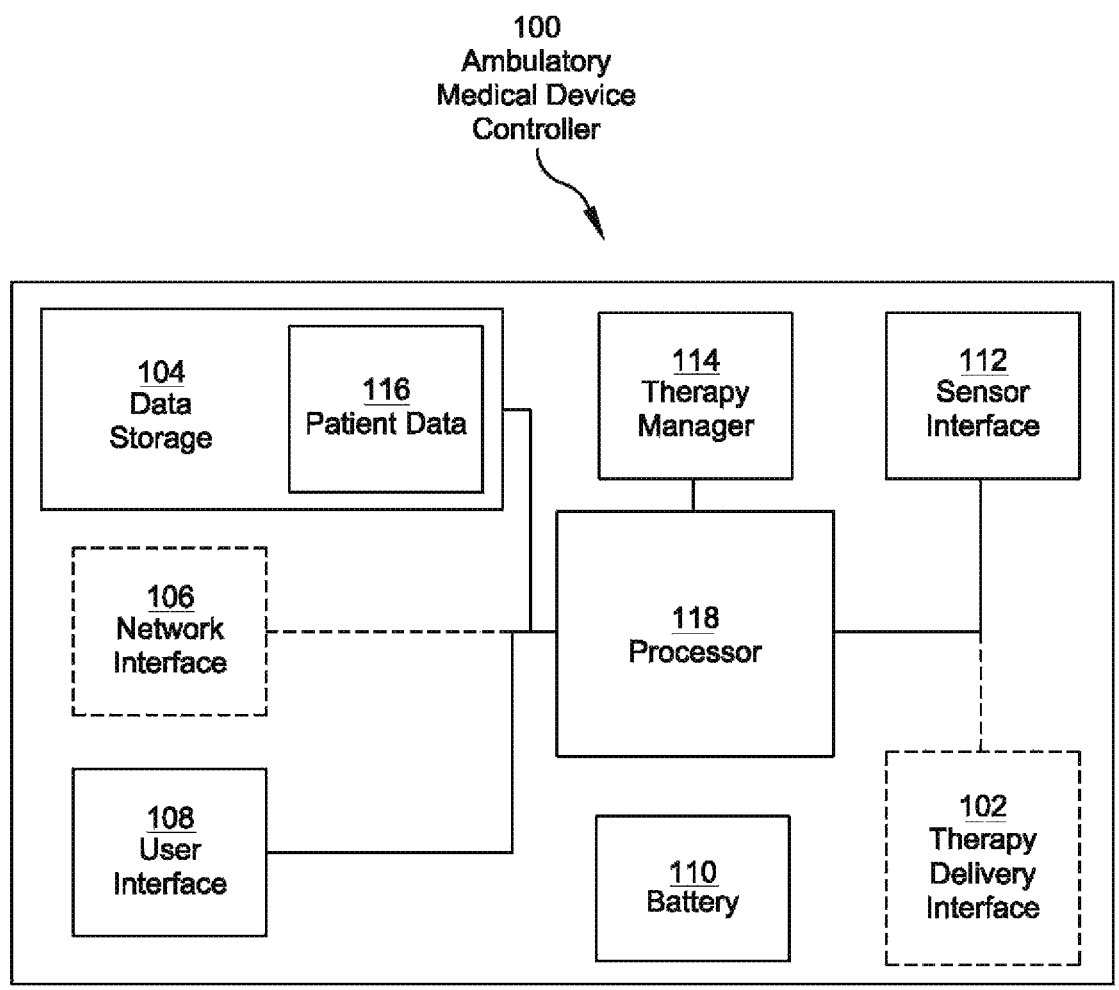
FIG. 1 is a functional schematic of one example of an ambulatory medical device controller.

Some embodiments disclosed herein relate generally to the administration of therapy to a patient using an ambulatory medical device. The ambulatory medical device may monitor any of a variety of physiological parameters to identify patient health disorders and provide therapy accordingly. The patient may, however, require delay or prevention of the therapy. In an embodiment, an ambulatory medical device has a response mechanism including two response buttons that the patient may push simultaneously to delay therapy. Requiring that a patient push both response buttons simultaneously substantially reduces the likelihood that the patient accidentally activated the response buttons to delay therapy, such as where the patient falls on the ground and activates a single response button.

Patients with illnesses that cause fine motor skills to deteriorate, such as diabetes and arthritis, may find it challenging to depress both response buttons simultaneously. Accordingly, in some embodiments, an ambulatory medical device is provided that is configured to accurately identify a state of patient responsiveness and delay therapy where input is received that indicates the patient is responsive. Examples of such input include a change in the status of one or more of the response mechanisms after issuance of a request to the patient to do so.

More specifically, in at least some embodiments, an ambulatory medical device is configurable to operate in at least two modes. The first mode may require the patient to only activate and/or deactivate a single response button. The first mode, however, may require a predefined sequence of activations and/or deactivations within specific time intervals to successfully delay the administration of therapy. Several examples of the predefined sequences performed in the first mode are described further below in the Example Patient Monitoring and Treatment Scenarios in a First Operating Mode section and FIGS. 5A-5D. The second mode may require the patient to activate two response buttons to successfully delay treatment. Several examples of the predefined sequences performed in the second mode are described further below in the Example Patient Monitoring and Treatment Scenarios in a Second Operating Mode section.

The examples of the methods and apparatus discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Ambulatory Medical Device Controller

FIG. 1 illustrates an ambulatory medical device controller 100 that is configured to monitor a patient and the patient's environment for events of interest and to delivery therapy to the patient as necessary. The ambulatory medical device controller 100 may, for example, be configured for use in a wearable defibrillator. As shown in FIG. 1, the ambulatory medical device controller 100 includes at least one processor 118, a sensor interface 112, a therapy manager 114, a therapy delivery interface 102, data storage 104, a communication network interface 106, a user interface 108, and a battery 110. The data storage 104 includes patient data 116. Further, in this illustrated example, the battery 110 is a rechargeable 3 cell 2200 mAh lithium ion battery pack that provides electrical power to the other device components with a minimum 24 hour runtime between charges. It is appreciated that some or all of the components described with regard to the ambulatory medical device controller 100 may be located within or are integral to a protective housing of the ambulatory device medical controller 100, such as the housing illustrated in FIGS. 6A and 6B.

According to the embodiment illustrated in FIG. 1, the processor 118 is coupled with the sensor interface 112, the therapy delivery interface 102, the data storage 104, the network interface 106, and the user interface 108. The processor 118 performs a series of instructions that result in manipulated data which are stored in and retrieved from the data storage 104. According to a variety of examples, the processor 118 is a commercially available processor such as a processor manufactured by Texas Instruments, Intel, AMD, Sun, IBM, Motorola, Freescale, and ARM Holdings. However, the processor 118 may be any type of processor, multiprocessor or controller, whether commercially available or specially manufactured. For instance, according to one example, the processor 118 may include a power conserving processor arrangement such as described in U.S. patent application Ser. No. 12/833,096, titled "SYSTEM AND METHOD FOR CONSERVING POWER IN A MEDICAL DEVICE," filed Jul. 9, 2010 (hereinafter the "096 application") (which issued as U.S. Pat. No. 8,904,214 on Dec. 2, 2014), which is hereby incorporated herein by reference in its entirety. In another example, the processor 118 is an Intel® PXA270.

In addition, in several embodiments the processor 118 is configured to execute a conventional real-time operating system (RTOS), such as RTLinux. In these examples, the RTOS may provide platform services to application software, such as some examples of the therapy manager 114, which is discussed further below. These platform services may include inter-process and network communication, file system management and standard database manipulation. One or more of many operating systems may be used, and examples may not be limited to any particular operating system or operating system characteristic. For instance, in some examples, the processor 118 may be configured to execute a non-real time operating system, such as BSD or GNU/Linux.

In some embodiments, the therapy manager 114 is configured to monitor at least one physiological parameter of a patient, detect health disorders, and administer therapy to the patient as necessary. Particular examples of the processes performed by the therapy manager 114 are discussed further below with reference to FIGS. 3-5 and within the Therapy Administration Processes section.

The therapy manager 114 may be implemented using hardware or a combination of hardware and software. For instance, in one example, the therapy manager 114 is implemented as a software component that is stored within the data storage 112 and executed by the processor 118. In this example, the instructions included in the therapy manager 114 program the processor 118 to monitor at least one physiological parameter of a patient, detect health disorders, and administer therapy to the patient as necessary. In other examples, therapy manager 114 may be an application-specific integrated circuit (ASIC) that is coupled with the processor 118 and tailored to monitor at least one physiological parameter of a patient, detect health disorders, and administer therapy to the patient as necessary. Thus, examples of the therapy manager 114 are not limited to a particular hardware or software implementation.

In some embodiments, the components disclosed herein, such as the therapy manager 114, may read configuration parameters that affect the functions performed by the components. These configuration parameters may be physically stored in any form of suitable memory including volatile memory, such as RAM, or nonvolatile memory, such as flash memory or a magnetic hard drive. In addition, the configuration parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 108, that allow external entities to modify the configuration parameters and thereby configure the behavior of the components.

The data storage 104 includes a computer readable and writeable nonvolatile data storage medium configured to store non-transitory instructions and data. In addition, the data storage 104 includes processor memory that stores data during operation of the processor 118. In some examples, the processor memory includes a relatively high performance, volatile, random access memory such as dynamic random access memory (DRAM), static memory (SRAM) or synchronous DRAM. However, the processor memory may include any device for storing data, such as a nonvolatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the nonvolatile storage medium after processing is complete. A variety of components may manage data movement between the nonvolatile storage medium and the processor memory and examples are not limited to particular data management components. Further, examples are not limited to a particular memory, memory system, or data storage system.

The instructions stored on the data storage 104 may include executable programs or other code that can be executed by the processor 118. The instructions may be persistently stored as encoded signals, and the instructions may cause the processor 118 to perform the functions described herein. The data storage 104 also may include information that is recorded, on or in, the medium, and this information may be processed by the processor 118 during execution of instructions. The medium may, for example, be optical disk, magnetic disk or flash memory, among others, and may be permanently affixed to, or removable from, the ambulatory medical device controller 100.

In some embodiments, the patient data 116 includes data used by the therapy manager 114 to monitor at least one physiological parameter of a patient, detect health disorders, and administer therapy to the patient as necessary. More particularly, according to the illustrated example, the patient data 116 includes information that identifies patient health disorder information and patient preferences. In an embodiment, the ambulatory medical device controller 100 is configurable between multiple modes of operation. The ambulatory medical device controller 100 may be configured by trained personnel during a patient fitting and training process when the ambulatory medical device is first issued to the patient. The patient may also reconfigure the ambulatory medical device controller 100 in the field after the initial fitting and training process. The configuration and/or reconfiguration process may include, for example, a specific activation sequence to change the mode of operation of the ambulatory medical device controller 100. One example of a configuration process that may be used to change the mode of operation of the ambulatory medical device controller 100 in the field is described within U.S. patent application Ser. No. 13/782,232, titled "SYSTEMS AND METHODS FOR CONFIGURING A WEARABLE MEDICAL MONITORING AND/OR TREATMENT DEVICE," filed Mar. 1, 2013 (which issued as U.S. Pat. No. 9,878,171 on Jan. 30, 2018), which is hereby incorporated herein by reference in its entirety.

In some embodiments, the ambulatory medical device controller 100 is configurable between two modes of operation. The first mode of operation allows the patient to delay the administration of therapy in response to changing the status of one or more response buttons within one or more predefined time intervals. The second mode of operation allows the patient to delay the administration of therapy in response to the patient changing the status of two or more response buttons simultaneously. The first mode of operation may be suitable for patients with poor dexterity or poor fine motor skills that find it difficult to push two or more response buttons simultaneously. Example treatment sequences performed by the ambulatory medical device controller 100 during operation in the first mode are described in the Example Patient Monitoring and Treatment Scenarios in a First Operating Mode section and FIGS. 5A-5D. The second mode of operation may allow the patient to delay the administration of therapy in response to the patient changing the status of two or more response buttons. Example treatment sequences performed by the ambulatory medical device controller 100 during operation in the second mode are described in the Example Patient Monitoring and Treatment Scenarios in a Second Operating Mode section.

In an embodiment, the ambulatory medical device controller 100 configures itself to operate in either the first or second mode of operation. For example, in some embodiments the ambulatory medical device controller 100 may be configured to operate in the second mode of operation (i.e., requires two buttons to be pushed simultaneously to delay therapy) and detect that the patient cannot fully depress both buttons simultaneously via one or more pressure sensors in each button. The ambulatory medical device controller 100 may then configure itself to operate in the first mode of operation (i.e., requires one button to be pushed to delay therapy). In other embodiments, the ambulatory device may detect alternating button pushes or repeated single button pushes and configure itself to operation in the first mode. It is appreciated that the ambulatory medical device controller may also include a self-test procedure. The self-test procedure, for example, may include requesting the patient to push both buttons and determine whether the first or second mode operation is appropriate for the particular patient.

It is appreciated that the first and second modes of operation may be applied to other ambulatory medical device controller operations outside of the delay of therapy administration. For example, power up self tests, health parameter recording (e.g., ECG), or any other activity may require the activation of one or more response buttons in the first mode while requiring the activation of two or more response buttons simultaneously in the second mode.

As illustrated in FIG. 1, the therapy manager 114 and the patient data 116 are separate components. However, in other examples, the therapy manager 114 and the patient data 116 may be combined into a single component or re-organized so that a portion of the data included in the therapy manager 114, such as executable code that causes the processor 118 to monitor at least one physiological parameter of a patient, detect health disorders, and administer therapy to the patient as necessary, resides in the patient data 116, or vice versa. Such variations in these and the other components illustrated in FIG. 1 are intended to be within the scope of the embodiments disclosed herein.

The patient data 116 may be stored in any logical construction capable of storing information on a computer readable medium including, among other structures, flat files, indexed files, hierarchical databases, relational databases or object oriented databases. These data structures may be specifically configured to conserve storage space or increase data exchange performance. In addition, various examples organize the patient data 116 into particularized and, in some cases, unique structures to perform the functions disclosed herein. In these examples, the data structures are sized and arranged to store values for particular types of data, such as integers, floating point numbers, character strings, arrays, linked lists, and the like.

As shown in FIG. 1, the ambulatory medical device controller 100 includes several system interface components 102, 106, and 112. Each of these system interface components is configured to exchange, i.e. send or receive, data with one or more specialized devices that may be located within the housing of the ambulatory medical device controller 100 or elsewhere. The interfaces 102, 106, and 112 may include hardware components, software components or a combination of both. Within each interface, these components physically and logically couple the ambulatory medical device controller 100 to the specialized devices. This physical and logical coupling enables the ambulatory medical device controller 100 to both communicate with and, in some instances, power or control the operation of the specialized devices. These specialized devices may include physiological sensors, therapy delivery devices, and computer networking devices. It is appreciated that the sensor interface 112 and the therapy delivery interface 102 may be combined to form a single sensor and therapy delivery interface.

According to various examples, the hardware and software components of the interfaces 102, 106 and 112 implement a variety of coupling and communication techniques. In some examples, the interfaces 102, 106, and 112 use leads, cables or other wired connectors as conduits to exchange data between the ambulatory medical device controller 100 and specialized devices. In other examples, the interfaces 102, 106, and 112 communicate with specialized devices using wireless technologies such as radio frequency or infrared technology. The software components included in the interfaces 102, 106, and 112 enable the processor 118 to communicate with specialized devices. These software components may include elements such as objects, executable code, and populated data structures. Together, these software components provide software interfaces through which the processor 118 can exchange information with specialized devices. Moreover, in at least some examples where one or more specialized devices communicate using analog signals, the interfaces 102, 106, and 112 further include components configured to convert analog information into digital information, and vice-versa, to enable the processor 118 to communicate with specialized devices.

As discussed above, the system interface components 102, 106, and 112 shown in the example of FIG. 1 support different types of specialized devices. For instance, the components of the sensor interface 112 couple the processor 118 to one or more physiological sensors such as a body temperature sensors, respiration monitors, acoustic sensors, and ECG electrodes (e.g., dry capacitive ECG electrodes), one or more environmental sensors such as atmospheric thermometers, airflow sensors, video sensors, audio sensors, accelerometers, GPS locators, and hygrometers. In these examples, the sensors may include sensors with a relatively low sampling rate, such as wireless sensors. An example acoustic sensor is described in U.S. patent application Ser. No. 14/314,799, titled "THERAPEUTIC DEVICE INCLUDING ACOUSTIC SENSOR," filed Jun. 25, 2014 (which issued as U.S. Pat. No. 9,955,938 on May 1, 2018), which is hereby incorporated herein by reference in its entirety.

The components of the therapy delivery interface 102 couple one or more therapy delivery devices, such as capacitors and defibrillator electrodes, to the processor 118. In addition, the components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, IEEE 802.15.4j, BLUETOOTH, ZigBee, M-Bus, CAN-bus, IP, IPV6, UDP, DTN, HTTP, FTP, SNMP, CDMA, NMEA and GSM. To ensure data transfer is secure, in some examples, the ambulatory medical device controller 100 can transmit data via the network interface 106 using a variety of security measures including, for example, TLS, SSL or VPN. In other examples, the network interface 106 includes both a physical interface configured for wireless communication and a physical interface configured for wired communication. According to various embodiments, the network interface 106 enables communication between the ambulatory medical device controller 100 and a variety of personal electronic devices including computer enabled glasses and earpieces.

Thus, the various system interfaces incorporated in the ambulatory medical device controller 100 allow the device to interoperate with a wide variety of devices in various contexts. For instance, some examples of the ambulatory medical device controller 100 are configured to perform a process of sending critical events and data to a centralized server via the network interface 106. An illustration of a process in accord with these examples is disclosed in U.S. Pat. No. 6,681,003, titled "DATA COLLECTION AND SYSTEM MANAGEMENT FOR PATIENT-WORN MEDICAL DEVICES," issued on Jan. 20, 2004, which is hereby incorporated herein by reference in its entirety.

As illustrated in FIG. 1, the therapy delivery interface 102 and the network interface 106 are optional and may not be included in every example. For instance, a heart rate monitor may employ the ambulatory medical device controller 100 to issue alarms but may not include a therapy delivery interface 102 to treat cardiac abnormalities. Similarly, an ambulatory defibrillator may include the ambulatory medical device controller 100 to provide alarm functionality but may not include a network interface 106 where, for example, the ambulatory defibrillator is designed to rely on the user interface 108 to announce alarms.

The user interface 108 shown in FIG. 1 includes a combination of hardware and software components that allow the ambulatory medical device controller 100 to communicate with an external entity, such as a patient or other user. These components may be configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, electrodes, touch screens, printing devices, display screens and speakers. In some examples, the electrodes include an illuminating element, such as an LED. In other examples, the printing devices include printers capable of rendering visual or tactile (Braille) output. It is appreciated that the user interface components described herein may be coupled with the user interface 108 of the ambulatory medical device controller 100 or included in the housing of the ambulatory medical device controller.

The ambulatory medical device controller 100 has a variety of potential applications and is well suited to devices that notify external entities of a variety of events, some of which require a predetermined response from the external entity. Predetermined responses may include any response that is appropriate given the event being reported. Predetermined responses may include acknowledgment of the alarm, entry of information indicating that the alarm is being addressed and rectification of the event or condition that triggered the alarm. Examples of devices to which the ambulatory medical device controller 100 is well suited include critical care medical devices, such as an ambulatory external defibrillator.

Example Ambulatory Medical Device

Figure 2:
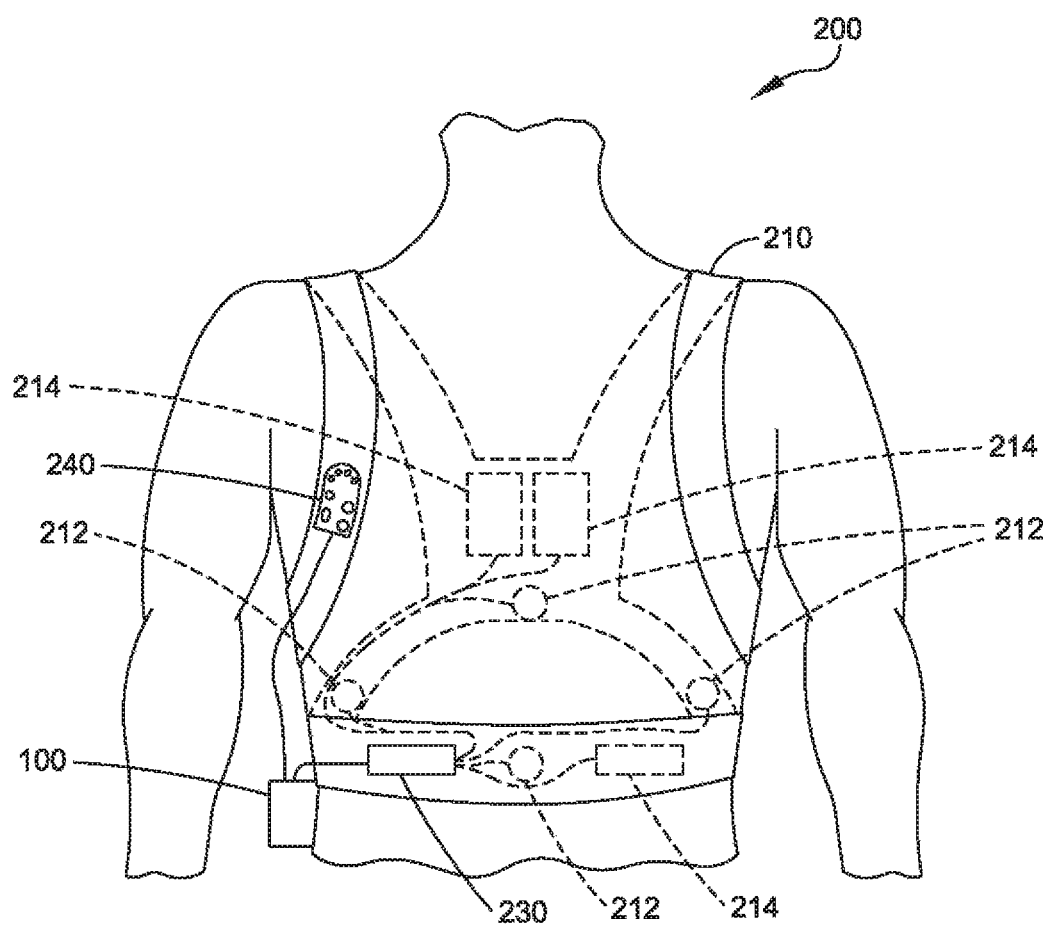
FIG. 2 is an illustration of one example of an ambulatory medical device.

In an embodiment, the ambulatory medical device is a wearable defibrillator that consists of a garment (e.g., a vest and/or belt) that is worn by the patient. The wearable defibrillator monitors the patient's ECG with sensing electrodes, detects life-threatening arrhythmias, and delivers a cardioverting or defibrillating shock through therapy electrodes if treatment is necessary. FIG. 2 illustrates a wearable defibrillator, such as a LifeVest® wearable cardioverter defibrillator available from ZOLL Medical Corporation of Chelmsford, Mass. As shown, the wearable defibrillator 200 includes a harness 210 having a pair of shoulder straps and a belt that is worn about the torso of a patient. The wearable defibrillator 200 includes a plurality of ECG sensing electrodes 212 that are attached to the harness 210 at various positions about the patient's body and electrically coupled with the sensor interface 112 of the ambulatory medical device controller 100 via a connection pod 230. The plurality of ECG sensing electrodes 212, which may be dry-sensing capacitance electrodes, long term wear adhesive electrodes, or conventional adhesive electrodes, are coupled with the ambulatory medical device controller 100 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 212 may be disposed at varying locations about the patient's body.

The wearable defibrillator 200 also includes a plurality of therapy electrodes 214 that are electrically coupled with the therapy delivery interface 102 of the ambulatory medical device controller 100 via the connection pod 230 and which are configured to deliver one or more therapeutic defibrillating shocks to the body of the patient, if it is determined that such treatment is warranted. The connection pod 230 electrically couples the plurality of ECG sensing electrodes 212 and the plurality of therapy electrodes 214 to the sensor interface 112 and the therapy delivery interface 102, respectively, of the ambulatory medical device controller 100, and may include electronic circuitry. The connection pod 230 may also include other electronic circuitry, such as a motion sensor or accelerometer through which patient activity may be monitored.

As shown in FIG. 2, the wearable defibrillator 200 also includes a user interface pod 240 that is electrically coupled with, or integrated with, the user interface 108 of the ambulatory medical device controller 100. The user interface pod 240 can be attached to the patient's clothing or to the harness 210, for example, via a clip (not shown) that is attached to a portion of the interface pod 240. Alternatively, the user interface pod 240 may simply be held in a person's hand. In some embodiments, the user interface pod 240 may communicate wirelessly with the user interface 108 of the ambulatory medical device controller 100, for example, using a BLUETOOTH, Wireless USB, ZigBee, Wireless Ethernet, GSM, or other type of communication interface. The user interface pod 240 typically includes a number of buttons by which the patient, or a bystander can communicate with the ambulatory medical device controller 100, and a speaker by which the ambulatory medical device controller 100 may communicate with the patient or the bystander. In one example, the interface pod has two response buttons that the patient may communicate with the ambulatory medical device controller 100 to delay the administration of therapy.

Figure 6B:
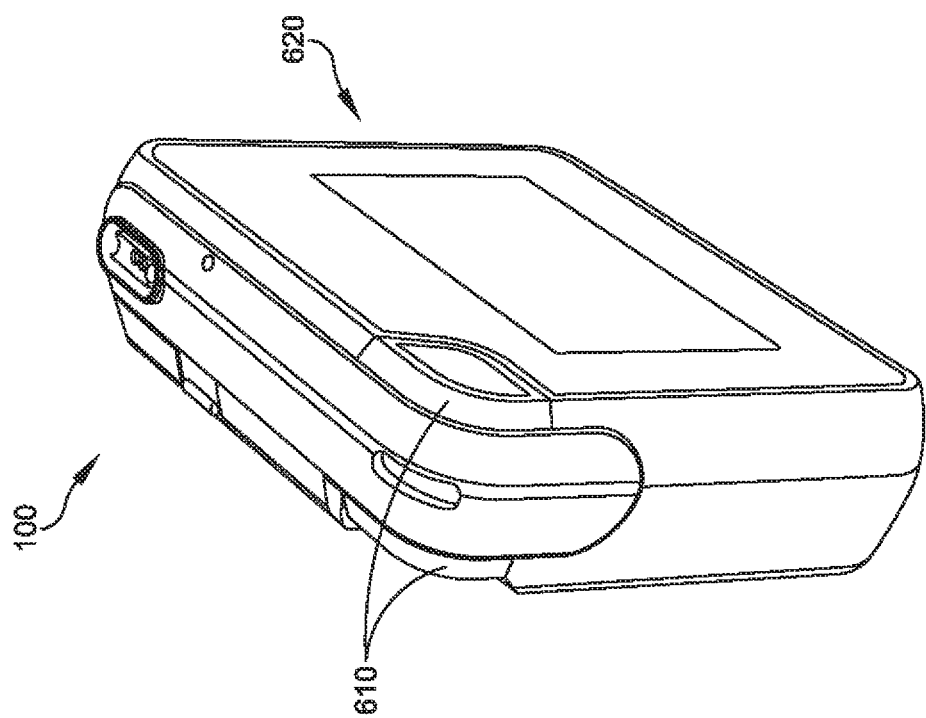
FIGS. 6A-B are illustrations of one example of an ambulatory medical device controller.
Figure 6A:
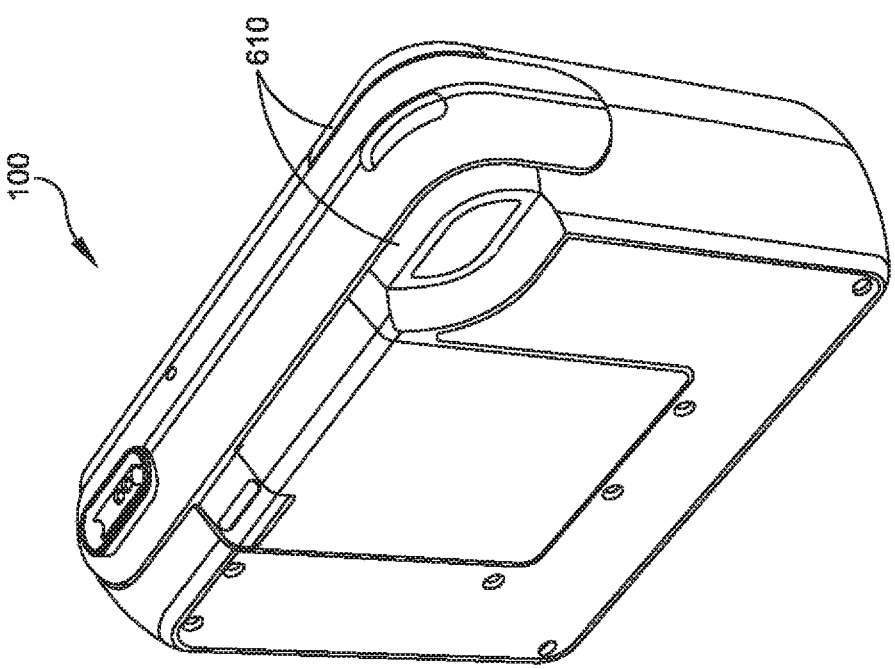

In another example, the functionality of the user interface pod 240 is integrated into the housing of the ambulatory medical device controller 100. FIGS. 6A-B illustrate such an example of the ambulatory medical device controller 100. The ambulatory medical device controller 100 includes a tactile response mechanism comprising two response buttons 610 on opposing sides of the housing of the ambulatory medical device controller 100. As shown in FIGS. 6A-B, the response buttons 610 are recessed below a plane of an outer surface of the housing to reduce the likelihood of accidental activation (e.g., a patient falling on and actuating the response button). The ambulatory medical device controller 100 also includes, in this example, a display screen 620 to enable the communication of visual stimuli to the patient. In addition, the display screen 620 may also incorporate a touch screen to enable the patient to interact with the ambulatory medical device controller 100. It is appreciated that the response buttons 610 do not have to be placed on opposing sides of the housing as illustrated in FIGS. 6A-B. The response buttons, for example, may be located adjacent to each other in the housing of the ambulatory medical device controller. The adjacent placement of the response buttons may make it easier for individuals with smaller hands or less dexterity to engage the response buttons.

Where the ambulatory medical device controller 100 determines that the patient is experiencing cardiac arrhythmia, the ambulatory medical device controller 100 may issue an audible alarm via a speaker and/or display a notification via the display screen 620 on the ambulatory medical device controller 100, or the user interface pod 240, alerting the patient and any bystanders to the patient's medical condition. The ambulatory medical device controller 100 may also instruct the patient to press and hold one or more response buttons 610 on the ambulatory medical device controller 100, or on the user interface pod 240, to indicate that the patient is conscious, thereby instructing the ambulatory medical device controller 100 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

It is appreciated that the response mechanism employed by the ambulatory medical device controller may not be limited to two response buttons. For example, the response mechanism of the ambulatory medical device controller 100 may incorporate one or more microphones to enable the ambulatory medical device controller 100 to receive voice commands from the patient. In this example, the ambulatory medical device controller 100 may request that the patient say a specific phrase to delay the administration of therapy.

Therapy Administration Processes

Figure 3:
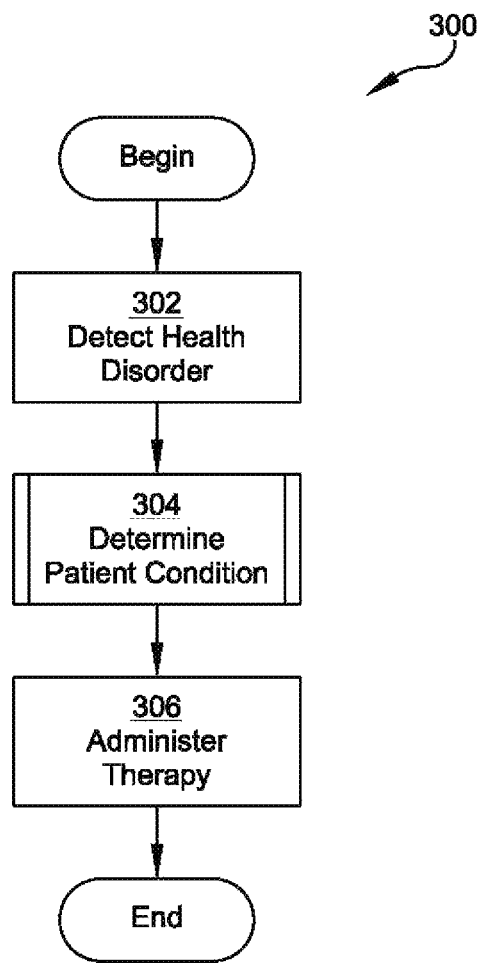
FIG. 3 is a flowchart of an example therapy delivery process.

Various embodiments implement and enable processes through which an ambulatory medical device controller, such as the ambulatory medical device controller 100 described above with reference to FIG. 1, administers therapy to a patient. FIG. 3 illustrates one such process 300 that includes acts of detecting a health disorder 302, determining patient condition 304, and administering therapy 306.

In the act 302, the ambulatory medical device controller detects a health disorder of the patient. In an embodiment, the act 302 includes monitoring at least one physiological parameter of the patient having at least one value potentially indicative of a health disorder. For example, the ambulatory medical device controller may monitor a cardiac rhythm of the patient and detect one or more heart arrhythmia health disorders. Specific examples of detectable heart arrhythmia health disorders include, but are not limited to, premature ventricular contraction, ventricular defibrillation, bradycardia, tachycardia (e.g., ventricular tachycardia, supraventricular tachycardia, and sinus tachycardia), an erratic heart rate with no discernible sinus rhythm, asystole, or pulseless electrical activity. The ambulatory medical device controller may use any of a variety of methods to detect health disorders. In one example, the ambulatory medical device controller stores information regarding normal readings of the physiological parameter. In this example, the ambulatory medical device controller includes signal processing capabilities and matches the incoming readings with the stored known normal patient readings that characterize the patient's normal cardiac function. The matching process could be implemented in a variety of methods including a matched filtering process. An example system and method for detecting health disorders relating to cardiac arrhythmias is described in U.S. patent application Ser. No. 13/428,329, titled "SELECTION OF OPTIMAL CHANNEL FOR RATE DETERMINATION," filed Mar. 23, 2013 (which issued as U.S. Pat. No. 8,897,860 on Nov. 25, 2014), which is hereby incorporated herein by reference in its entirety. Another example system and method for detecting health disorders relating to cardiac arrhythmias is described in U.S. Pat. No. 8,706,215, titled "WEARABLE AMBULATORY MEDICAL DEVICE WITH MULTIPLE SENSING ELECTRODES," issued Apr. 22, 2014, which is hereby incorporated herein by reference in its entirety.

In the act 304, the ambulatory medical device controller determines a patient condition. Determining the patient condition may include identifying a state of responsiveness of the patient. Actions performed by the ambulatory medical device controller during execution of the act 304 are described further below with reference to FIG. 4.

In the act 306, the ambulatory medical device controller administers therapy to the patient. In some examples where the ambulatory medical device controller is coupled with one or more therapy electrodes, the ambulatory medical device controller delivers one or more therapeutic shocks to the patient. After the act 306, the ambulatory medical device controller terminates the process 300. It is appreciated that the ambulatory medical device controller may execute the process 300 again if the initial administration of therapy did not resolve all of the health disorders of the patient.

Figure 4:
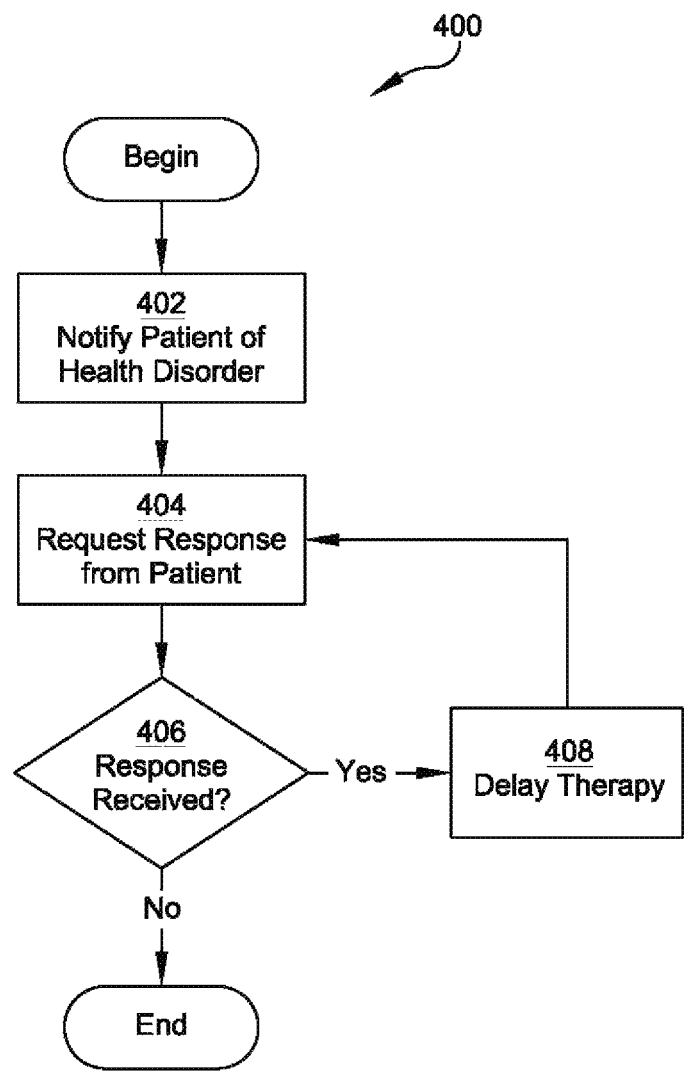
FIG. 4 is a flowchart of an example process to determine patient condition.

As discussed above with regard to the act 304 in FIG. 3, various embodiments implement processes for determining patient condition (e.g., identifying a state of responsiveness of the patient). FIG. 4 illustrates one such process 400 that implements the act 304 and that includes acts of notifying the patient of a health disorder 402, requesting a response from the patient 404, determining whether the response was received 406, and delaying therapy if the response was received 408.

In the act 402, the ambulatory medical device controller notifies the patient of the health disorder. In one example, the ambulatory medical device controller, through the user interface 108, displays a patient notification on a display screen, transmits an audible alert via a speaker to the patient or both. The audible alert may include a siren or specific alerts stated by a voice that notify the patient audibly. In other examples, a tactile stimulator is housed in or coupled with the ambulatory medical device controller to notify the patient. The tactile stimulator may include a motor with an unbalanced weight on its shaft. When the motor is on, it causes the belt to vibrate much like a cell-phone in vibration mode. It is appreciated that the tactile stimulator may be activated by the ambulatory medical device controller during any patient notification, alert, or siren.

In the act 404, the ambulatory medical device controller requests a targeted response from the patient. The response from the patient is received by a response mechanism of the ambulatory medical device controller. In an embodiment, the response mechanism comprises two response buttons coupled with or integrated with the ambulatory medical device. The patient may communicate with the ambulatory medical device controller through activating or deactivating one or both of the response buttons. In the act 404, the ambulatory medical device controller requests that the patient change the status of one response button (e.g., change the response button from a deactivated state to an activated state or vice-versa) within a predetermined amount of time. If the patient successfully performs the requested response, the ambulatory medical device may request that the patient again change the status of the same response button within another predetermined amount of time. Such sequences of requests and responses may be repeated one or more times to ensure the patient does not require treatment.

It is appreciated that a change in status of both response buttons may be recorded by the medical device controller as a successful patient response. In other embodiments, the ambulatory medical device controller may require any number of response button changes prior to recording a successful patient response and delaying the administration of therapy to the patient. It is also appreciated that the ambulatory medical device controller may include any number of response buttons and may request that the patient push any combination of response buttons to delay the administration of therapy.

In another embodiment, the response mechanism includes a touch screen coupled with or integrated with the ambulatory medical device controller. The patient communicates with the ambulatory medical device controller by interacting with the touch screen. For example, the patient may press a button displayed on the touch screen of the ambulatory medical device. If the patient successfully touches the button on the touch screen, the ambulatory medical device may relocate the button on the touch screen and request that the patient press the relocated button on the touch screen again.

In other embodiments, the response mechanism includes patient voice recognition through one or more microphones coupled with or integrated with the ambulatory medical device controller. For example, in one embodiment, the ambulatory medical device controller may request the patient say a specific phrase to the ambulatory medical device controller.

In the act 406, the ambulatory medical device controller determines whether the requested action was performed. In an embodiment, the ambulatory medical device controller notifies the patient that administration of the therapy will be delayed or canceled when the patient successfully performs the requested action in two instances in succession. This notification may include any combination of audible, visual, and tactile output. In some embodiments, the ambulatory medical device controller determines whether the administration of the therapy is delayed or canceled based on a value of a predefined configuration parameter.

In another embodiment, the act 406 further includes reading one or more accelerometers communicatively connected to or integrated with the ambulatory medical device controller. The readings from the one or more accelerometers may be used to determine a state of consciousness of the patient through the detection of targeted patient activity. The ambulatory medical device controller may delay the administration of therapy responsive to detecting a conscious patient (e.g., detecting targeted patient activity). For example, the accelerometers may detect that the patient is walking and delay the administration of therapy. This delay of the administration of therapy responsive to patient activity may be independent of the requested action (e.g., change the status of a response button) or, where the patient responds with the requested action, may further increase the delay that would have resulted from the patient solely successfully performing the requested action. It is appreciated that the accelerometer may be employed by the ambulatory medical device controller to detect a patient fall and shorten delays and/or administer therapy to the patient responsive to the detected patient fall. In addition, other sensors may be used to determine the state of consciousness of the patient including, but not limited to, a microphone to detect patient speech, an acoustic sensor to detect viable respiration, and two or more response mechanisms that require patient activation (e.g., in the second mode of operation described herein).

As described above, in some embodiments, one or more response buttons are coupled with or integrated in the ambulatory medical device controller. In these embodiments, the ambulatory medical device controller monitors the status of the response buttons within the act 406. The ambulatory medical device controller may ignore a specific response button in the event that the button remains in an activated state for a period of time longer than a predetermined duration (e.g., the button is jammed where, for example, the patient has fallen on the controller in a manner in which the button is held in an activated state).

In another embodiment, the ambulatory medical device controller is configured to determine whether any actions requested and performed are performed by the patient. The ambulatory medical device may make this determination with reference to a body marker transmitted through the patient from the response button to electrodes on the patient such as described in U.S. Pat. No. 8,271,082, titled "MEDICAL DEVICE CONFIGURED TO TEST FOR USER RESPONSIVENESS," issued on Sep. 18, 2012, which is hereby incorporated herein by reference in its entirety. In embodiments where the patient is requested to audibly reply to the ambulatory medical device controller, patient voice recognition may be employed as described in U.S. Pat. No. 8,369,944 titled "WEARABLE DEFIBRILLATOR WITH AUDIO INPUT/OUTPUT," issued on Feb. 5, 2013, which is hereby incorporated herein by reference in its entirety.

After the therapy has been delayed in the act 408, the ambulatory medical device controller repeats the act 404 to ensure the patient remains conscious. A specific length of the delay may be selected responsive to the severity of the health disorder. In an embodiment, the ambulatory medical device controller monitors the cardiac rhythm of a patient to detect arrhythmias The ambulatory medical device controller may detect, for example, ventricular tachycardia and set the delay to 30 seconds. When the ambulatory medical device controller detects a health disorder that is more severe, for example ventricular fibrillation, the ambulatory medical device controller may shorten the delay to 15 seconds. It is appreciated that the cycle of requesting a specific action from the patient and delaying therapy accordingly may be limited to a finite number of cycles before automatically delivering therapy. Referring back to the act 406, the ambulatory medical device controller will proceed to complete the process 400 if the patient does not respond as required or has successfully delayed therapy up to a maximum predetermined amount of time. It is also appreciated that the ambulatory medical device controller may terminate the process 300 or the process 400 when the ambulatory medical device controller ceases to detect a health disorder of the patient for a predetermined period of time.

Each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely an ambulatory medical device controller configured to operate in one or more modes of operation according to the examples disclosed herein.

Example Patient Monitoring and Treatment Scenarios in a First Operating Mode

Various embodiments implement and enable various scenarios through which an ambulatory medical device controller operating in a first operating mode, such as the ambulatory medical device controller 100 described above with reference to FIG. 1, administers therapy to a patient. In some embodiments, the first mode of operation allows the patient to delay the administration of therapy in response to changing the status of one or more response buttons within one or more predefined time intervals. FIGS. 5A-D illustrate timelines of example treatment sequences for the administration of therapy (e.g., a defibrillating shock) to a patient by the ambulatory medical device controller while operating in a first operation mode. These treatment sequences include a cardiac rhythm monitoring sequence 502 with cardiac rhythm detection activities 516A-D, a arrhythmia declaration sequence 504 with arrhythmia declaration activities 518A-D, a response button sequence 506 with response button activities 520A-D, a screen sequence 508 with patient notification activities 522A-C, an audio and tactile sequence 510 with a vibrate activity 524, a siren activity 526, and alert activities 528A-D, a converter sequence 512 with a converter on activity 530, a converter off activity 532, an apply gel activity 534, and a transmit pulse activity 536, and an elapsed time sequence 514.

Figure 5A:
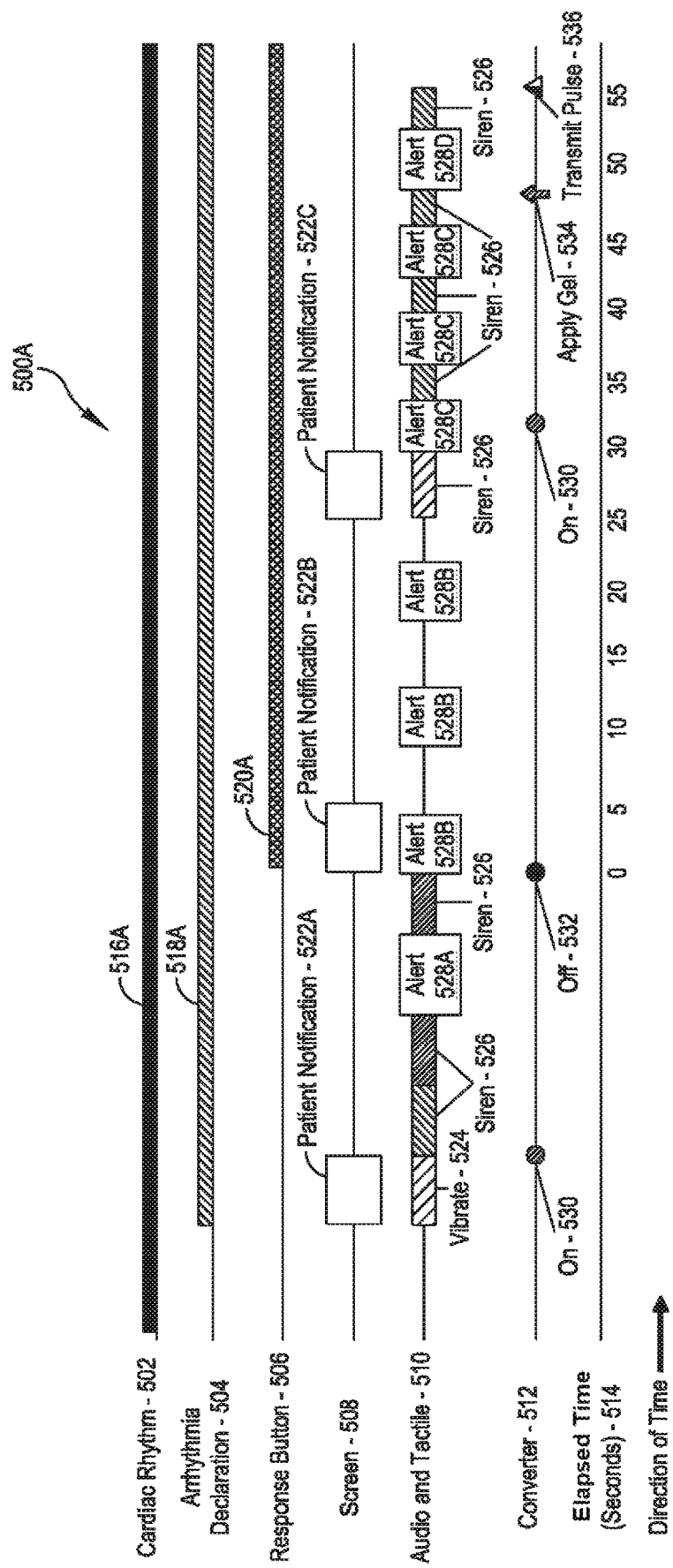
FIGS. 5A-D are timelines of example treatment sequences.

In a scenario 500A illustrated in FIG. 5A, the cardiac rhythm of a patient is continuously monitored in an activity 516A as seen on the cardiac rhythm sequence 502. The ambulatory medical device controller detects a cardiac arrhythmia event 518A seen on the arrhythmia declaration sequence 504. The ambulatory medical device controller subsequently displays a patient notification during patient notification activity 522A on the screen sequence 508. The patient notification may display text, for example, stating "Patient Respond." During this patient notification, the ambulatory medical device controller vibrates during vibrate activity 524 on the audio and tactile sequence 510. The vibrate activity 524 (e.g., vibrating the ambulatory medical device controller and/or a tactile stimulator disposed in the connection pad 230) and the display patient notification activity 522A are followed by sirens during siren activity 526 on the audio and tactile sequence 510. While the ambulatory medical device controller is alerting the patient through sirens, the converter turns on during converter on activity 530 on the converter sequence 512 in preparation for the administration of a therapeutic shock to the patient. Turning the converter on may enable a capacitor bank configured to deliver a large amount of energy to the patient through a therapeutic shock to charge from a battery source in the ambulatory medical device controller.

An audible alert activity 528A is then communicated to the patient and is followed by a siren activity 526 as shown on the audio and tactile sequence 510. For example, the ambulatory medical device controller may state "press response button to delay treatment" in the event that the response button's initial state is deactivated as shown in response button activity 520A on the response button sequence 506. The patient then responds accordingly to the patient notification activity 522A and the audible alert activity 528A and pushes the response button at the zero second mark on the elapsed time sequence. The converter is turned off during a converter off activity 532 as shown on the converter sequence 512 shortly after the zero second mark. In response to the patient's response and turning off the converter, the ambulatory medical device controller proceeds to notify the patient at the zero second mark through the patient notification activity 522B and the corresponding alert activity 528B that the patient has successfully completed the requested response. The patient notification activity 522B may display "treatment being delayed" and the audible alert activity 528B may recite "treatment has been delayed, bystanders do not interfere." The delay proceeds for approximately 25 seconds punctuated by the repeated audible alert activities 528B to the patient because the response button remains in an active state.

After about 25 seconds (i.e., at or about the 25 second mark of the elapsed time sequence 514), the ambulatory medical device controller requests an additional action be performed by the patient to verify patient responsiveness. The ambulatory medical device controller issues a patient notification during the patient notification activity 522C and may display "please let go of response button" as shown on the screen sequence 508. This notification is accompanied by siren activity 526 followed by an alert activity 528C that may state "please let go of response button" as shown on the audio and tactile sequence 510. The ambulatory medical device controller then turns on the converter in converter on activity 530 shortly after the 30 second mark of the elapsed time sequence 514 to ready the ambulatory medical device controller to deliver a therapeutic shock. The audible alert activities 528C and siren activities 526 continue until shortly after the 45 second mark on the elapsed time sequence 514 where gel is applied during the apply gel activity 534 on the converter sequence 512. The gel may be applied from therapy electrodes coupled with the ambulatory medical device controller to improve the transfer of energy from the therapy electrodes to the patient during the administration of the therapeutic shock. The ambulatory medical device controller proceeds to issue an audible alert during an alert activity 528D that may state "bystanders, do not touch patient" as shown on the audio and tactile sequence 510. The ambulatory medical device controller proceeds to transmit a defibrillating pulse of energy during the transmit pulse activity 536 as shown on the converter sequence 512 at the 55 second mark on the elapsed time sequence 514. It is appreciated that a second pulse may be transmitted if the arrhythmia continues and the patient fails to respond to additional requests from the ambulatory medical device controller.

Figure 5B:
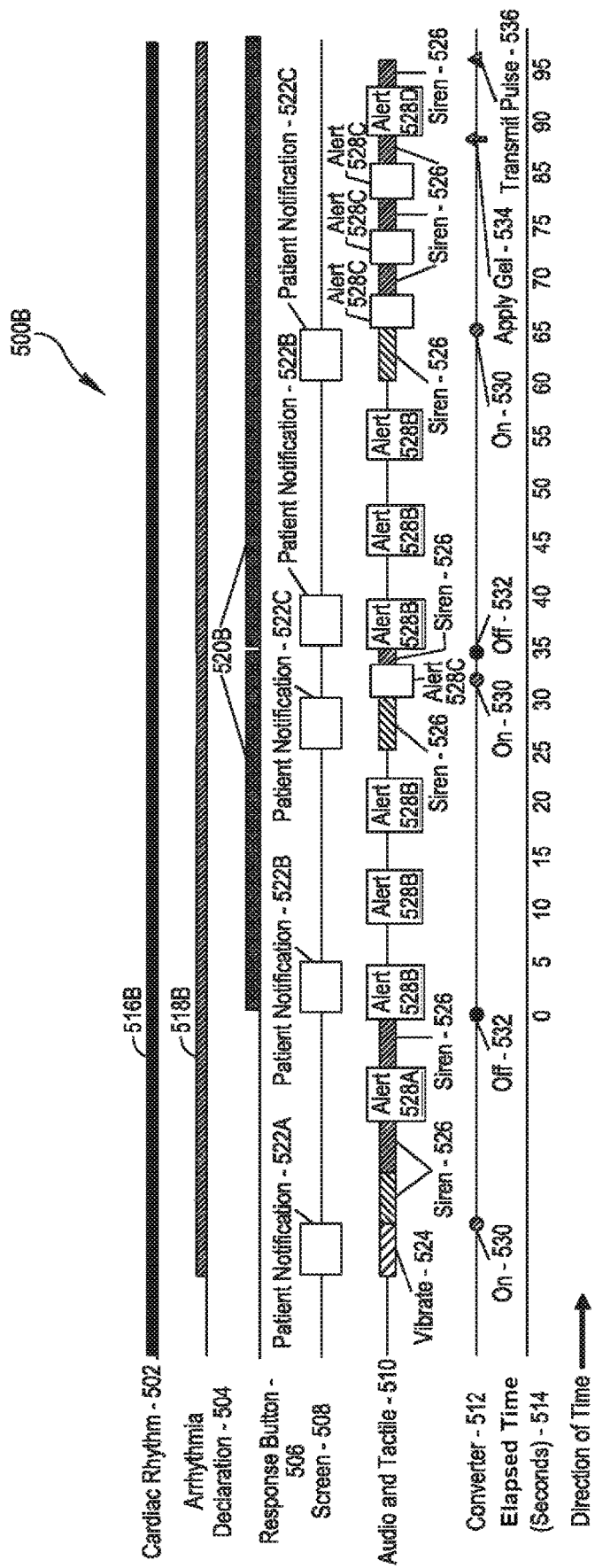

In scenario 500B of FIG. 5B, the cardiac rhythm of a patient is continuously monitored in an activity 516B and a cardiac arrhythmia event 518B occurs similar to scenario 500A as described above with regard to FIG. 5A. The ambulatory medical device controller executes the same initial process of issuing a patient notification 522A, an audible alert activity 528A, a vibrate activity 524, and a siren activity 526 prior to requesting the patient to push the response button in a patient notification activity 522B and an alert activity 528B. The ambulatory medical device controller delays the administration of therapy in response to the requested action (e.g., pushing the response button) being successfully completed by the patient. Next, the ambulatory device controller requests that the patient release the response button via a patient notification activity 522C and an alert activity 528C between the 25 and 30 second marks on the elapsed time sequence 514. At about the 35 second mark of the elapsed time sequence 514, the patient releases the response button and subsequently activates the response button as shown in a response button activity 520B on the response button sequence 506. The ambulatory medical device controller subsequently notifies the patient that the response was successfully performed as shown through a patient notification activity 522B and an alert activity 528B shortly after the 35 second mark of the elapsed time sequence 514. The ambulatory medical device controller proceeds to delay 25 seconds (i.e., until the 60 second mark on the elapsed time sequence 514) prior to asking the patient to release the response button through a patient notification activity 522C and a corresponding alert activity 528C. In this scenario, however, the response button is not released as shown in the responsive button activity 520B of the response button sequence. The patient may have fallen unconscious and accidentally fallen on the response button. The ambulatory medical device controller accordingly administers therapy using the same sequence as described with regard to scenario 500A but between the 65 and 95 second marks on the elapsed sequence 514 of FIG. 5B. It is appreciated that a second pulse may be transmitted if the arrhythmia continues and the patient fails to respond to additional requests from the ambulatory medical device controller.

Figure 5C:
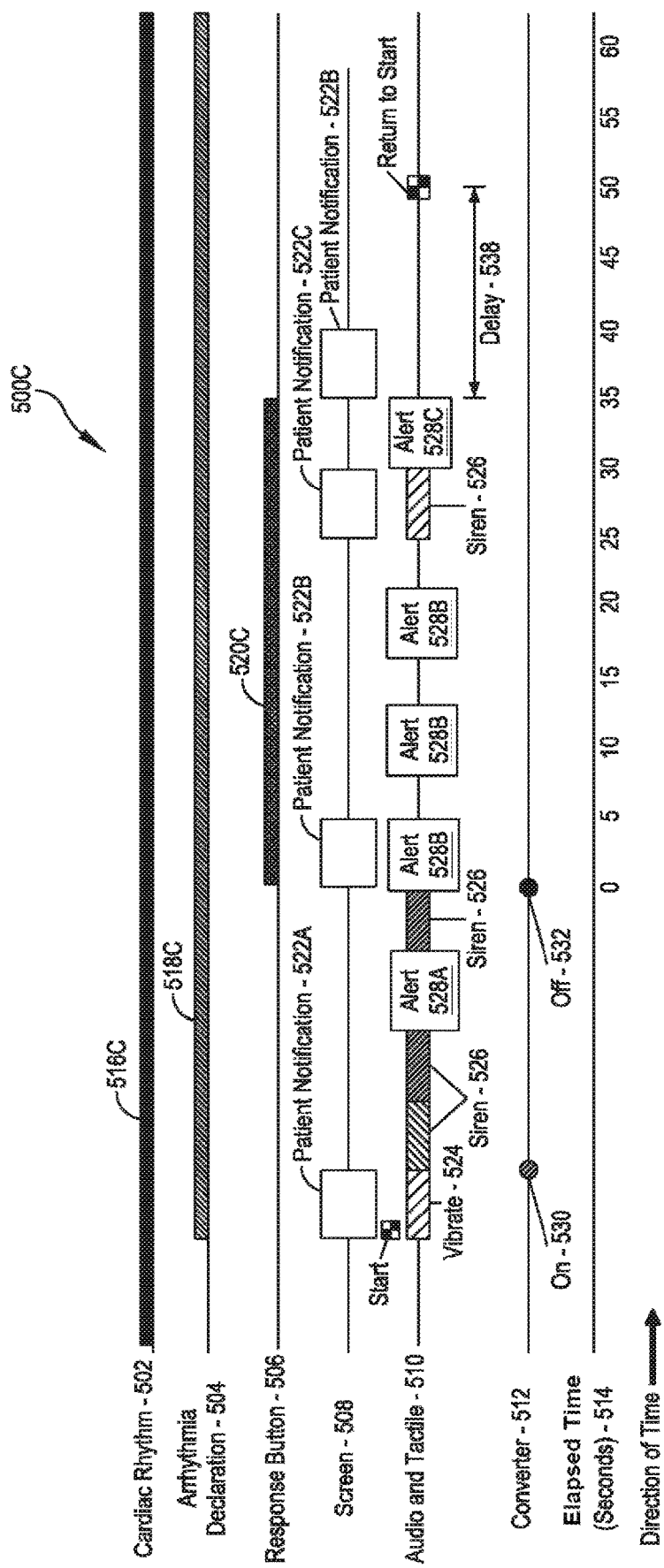

In scenario 500C of FIG. 5C, the cardiac rhythm of a patient is monitored in an activity 516C and a cardiac arrhythmia event 518C occurs similar to scenario 500A as described above with regard to FIG. 5A. The ambulatory medical device controller executes the same initial process of issuing a patient notification activity 522A, an audible alert activity 528A, a vibrate activity 524, and siren activities 526 prior to requesting the patient to push the response button in a patient notification activity 522B and an alert activity 528B. The ambulatory medical device controller delays the administration of therapy in response to the requested action (e.g., pushing the response button) being successfully completed by the patient. Next, the ambulatory device controller requests that the patient release the response button via a patient notification activity 522C and an alert activity 528C between the 25 and 30 second marks on the elapsed time sequence 514. The release of the response button at the 35 second mark on the elapsed time sequence occurs shortly after the ambulatory medical device controller requests the release of the response button. The device subsequently delays the administration of therapy 538 a period of time before repeating the process (e.g., beginning with a patient notification activity 522A and a vibrate activity 524). The length of the delay may be based upon the detected health disorder of the patient. In some embodiments, the ambulatory medical device controller is configured to delay the administration of therapy 15 seconds for ventricular defibrillation disorders and 30 seconds for ventricular tachycardia disorders.

Figure 5D:
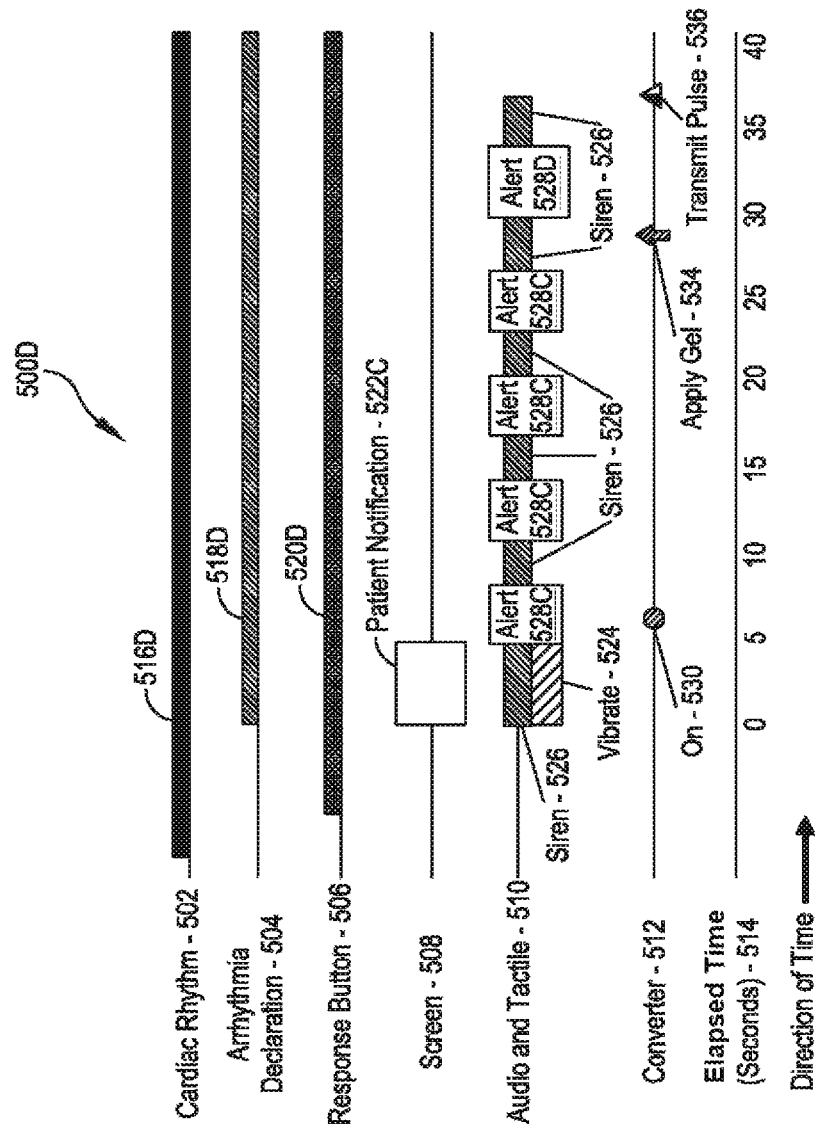

In scenario 500D of FIG. 5D, the cardiac rhythm of a patient is continuously monitored in an activity 516D. The ambulatory medical device controller detects a cardiac arrhythmia event 518D. As shown in response button activity 520D on the response button sequence 506, the ambulatory medical device controller detects that the response button is already in the activated position when the arrhythmia is detected at the event 518D. The ambulatory medical device controller subsequently issues a patient notification activity 522C requesting the patient to release the response button. The patient notification activity 522C is accompanied by siren activity 526 and a vibrate activity 524 followed by an audible alert activity 528C requesting the patient release the response button. In this scenario, the patient fails to response to the audible and visual requests to release the response button, and the ambulatory medical device controller consequently delivers therapy to the patient using a similar sequence as previously described with regard to scenario 500A between the 25 and 55 second marks on the elapsed sequence 514 of FIG. 5A. It is appreciated that a second pulse may be transmitted if the arrhythmia continues and the patient fails to respond to additional requests from the ambulatory medical device controller. While the example scenarios disclosed herein recite specific treatment sequences, the treatment sequences in each scenario may be altered without departing from the scope of the embodiments disclosed herein. For example, the activated and deactivated states of the response button may be interchanged.

It is appreciated that the treatment sequences described with reference to the first mode of operation and FIGS. 5A-D are not limited to ambulatory medical device controllers operating in the first mode of operation or ambulatory medical device controllers with multiple modes of operation. The treatment sequences may be applied to ambulatory medical device controllers operating in any mode of operation (e.g., the second mode of operation described herein). In addition, the response button may be replaced with one or more other response mechanisms. Other possible response mechanisms include, for example, a button on the touch screen and patient voice recognition.

Example Patient Monitoring and Treatment Scenarios in a Second Operating Mode

Various embodiments implement and enable various scenarios through which an ambulatory medical device controller operating in the second operating mode, such as the ambulatory medical device controller 100 described above with reference to FIG. 1, administers therapy to a patient. In some embodiments, the second mode of operation allows the patient to delay the administration of therapy in response to changing the status of two or more response buttons.

In some embodiments, the ambulatory medical device controller detects an arrhythmia and requests the patient to depress two buttons simultaneously. In these embodiments, the ambulatory medical device controller delays administration of therapy responsive to the activation of two response buttons simultaneously or within a predetermined period of time. The therapy may be delayed responsive to the patient activating both response buttons.

In an embodiment, the ambulatory medical device controller delays the administration of therapy until the patient releases one or two of the buttons. If the patient releases one or two of the response buttons, the ambulatory medical device controller may request that the patient push two response buttons again. Otherwise, the ambulatory medical device controller may administer therapy to the patient.

It is appreciated that the treatment sequences described with reference to the second operation mode may not be limited to ambulatory medical device controllers operating in the second mode of operation or ambulatory medical device controllers with multiple modes of operation. The treatment sequences may be applied to ambulatory medical device controllers operating in any mode of operation (e.g., the first mode of operation). In addition, the response button may be replaced with one or more other response mechanisms. Other possible response mechanisms include a button on the touch screen and patient voice recognition.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. An ambulatory medical device capable of delivering therapy to a patient, the ambulatory medical device comprising:
   a response mechanism comprising at least two buttons, wherein the response mechanism is configured to be activated by at least one of actuation of the at least two buttons and actuation of one of the at least two buttons;
   a controller operatively connected with the response mechanism, the controller including at least one processor coupled with a memory; and
   a therapy manager component executable by the controller and configured to:
      detect a physiological parameter having a value indicative of a health disorder of the patient;
      notify the patient of impending therapy delivery in response to the detection of the physiological parameter;
      monitor for activation of one of the at least two buttons of the response mechanism within at least one predetermined time period;
      monitor for activation of two of the at least two buttons of the response mechanism within the at least one predetermined time period;
      delay delivery of a therapy to the patient in response to detection of either
         activation of the one of the at least two buttons of the response mechanism within the at least one predetermined time period, or
         activation of the two of the at least two buttons of the response mechanism within the at least one predetermined time period; and
      prepare to deliver the therapy to the patient in response to each of the at least two buttons of the response mechanism remaining in a deactivated state until expiration of the at least one predetermined time period.

2. The ambulatory medical device of claim 1, wherein the therapy manager component executable by the controller is configured to request an additional action be performed by the patient to verify patient responsiveness.

3. The ambulatory medical device of claim 2, wherein the requested additional action comprises releasing either the activated one of the at least two buttons or the activated two of the at least two buttons of the response mechanism.

4. The ambulatory medical device of claim 1, wherein the therapy manager component is further configured to:
   monitor for activation of one of the at least two buttons of the response mechanism within a second predetermined time period;
   monitor for activation of two of the at least two buttons of the response mechanism within the second predetermined time period:
   request the patient release the one of the at least two buttons or release the two of the at least two buttons in response to detection of the activation of either the one of ef the at least two buttons or the activation of the two of the at least two buttons of the response mechanism remaining unchanged within the second predetermined time period; and
   either further delay delivery of the therapy in response to detection of a release of the one of the at least two buttons or a release of the two of the at least two buttons of the response mechanism within the second predetermined time period or prepare to deliver the therapy to the patient in response to the activation of the one of the at least two buttons or the activation of the two of the at least two buttons of the response mechanism remaining unchanged until expiration of the second predetermined time period.

5. The ambulatory medical device of claim 4, wherein the second predetermined time period comprises a range of 25 seconds to 60 seconds.

6. The ambulatory medical device of claim 1, wherein the response mechanism is integrated with the controller.

7. The ambulatory medical device of claim 1, wherein the ambulatory medical device includes a touch screen integrated with the controller, and the response mechanism includes a button displayed on the touch screen.

8. The ambulatory medical device of claim 1, further comprising a garment worn about a torso of the patient.

9. The ambulatory medical device of claim 1, wherein the response mechanism is coupled with the controller.

10. The ambulatory medical device of claim 1, wherein the therapy manager component is configured to notify the patient via at least one of audible, visual, and tactile output.

11. The ambulatory medical device of claim 3, wherein the therapy manager component is further configured to generate at least one of siren activity and vibration activity to accompany the request that the patient release the one of the at least two buttons response buttons.

12. The ambulatory medical device of claim 1, further comprising at least one capacitor coupled to a power converter and wherein the therapy manager component is configured to prepare to deliver the therapy at least in part by directing the power converter to charge the at least one capacitor.

13. The ambulatory medical device of claim 1, further comprising at least one gel deployment device and wherein the therapy manager component is configured to prepare to deliver the therapy at least in part by directing the at least one gel deployment device to deploy gel.

14. The ambulatory medical device of claim 4, further comprising at least one therapy pad and wherein the therapy manager component is configured to provide at least one therapeutic shock to the patient via the at least one therapy pad in response to either the one of the at least two buttons or the two of the at least two buttons of the response mechanism remaining activated until expiration of the second predetermined time period.

15. The ambulatory medical device of claim 1, wherein the at least two buttons are on opposite sides of a housing of the ambulatory medical device.

16. The ambulatory medical device of claim 15, wherein the at least two buttons are recessed below a plane of an outer surface of the housing.

17. The ambulatory medical device of claim 1, wherein the at least two buttons are located adjacent each other on a housing of the ambulatory medical device.

18. The ambulatory medical device of claim 1, wherein the at least one processor is further configured to cause a speaker of the ambulatory medical device to communicate an audible alert to bystanders to not touch the patient prior to transmitting a defibrillating pulse of energy.

19. The ambulatory medical device of claim 1, further comprising a motion sensor or accelerometer through which patient activity may be monitored.

20. An ambulatory medical device capable of delivering therapy to a patient, the ambulatory medical device comprising:
   a response mechanism comprising at least two buttons, wherein the response mechanism is configured to be activated by at least one of actuation of the at least two buttons and actuation of one of the at least two buttons;
   a controller operatively connected with the response mechanism, the controller including at least one processor coupled with a memory; and
   a therapy manager component executable by the controller and configured to:
      detect a physiological parameter having a value indicative of a health disorder of the patient;
      notify the patient of impending therapy delivery in response to the detection of the physiological parameter;
      monitor for activation of one of the at least two buttons of the response mechanism within at least one predetermined time period;
      monitor for activation of two of the at least two buttons of the response mechanism within the at least one predetermined time period;
      delay delivery of a therapy to the patient in response to detection of either
         activation of the one of the at least two buttons of the response mechanism within the at least one predetermined time period, or
         activation of the two of the at least two buttons of the response mechanism within the at least one predetermined time period;
      monitor for activation of one of the at least two buttons of the response mechanism within a second predetermined time period;
      monitor for activation of two of the at least two buttons of the response mechanism within the second predetermined time period:
      request the patient release the one of the at least two buttons or release the two of the at least two buttons in response to detection of the activation of either the one of the at least two buttons or the activation of the two of the at least two buttons of the response mechanism remaining unchanged within the second predetermined time period; and
      either further delay delivery of the therapy in response to detection of a release of the one of the at least two buttons or a release of the two of the at least two buttons of the response mechanism within the second predetermined time period or prepare to deliver the therapy to the patient in response to the activation of the one of the at least two buttons or the activation of the two of the at least two buttons of the response mechanism remaining unchanged until expiration of the second predetermined time period.

21. The ambulatory medical device of claim 20, wherein the second predetermined time period comprises a range of 25 seconds to 60 seconds.

22. The ambulatory medical device of claim 20, wherein the therapy manager component is configured to notify the patient via at least one of audible, visual, and tactile output.

23. The ambulatory medical device of claim 20, wherein the therapy manager component is further configured to generate at least one of siren activity and vibration activity to accompany the request that the patient release the one of the at least two buttons or release the two of the at least two buttons.

24. The ambulatory medical device of claim 20, further comprising at least one capacitor coupled to a power converter and wherein the therapy manager component is configured to prepare to deliver the therapy at least in part by directing the power converter to charge the at least one capacitor.

25. The ambulatory medical device of claim 20, further comprising at least one gel deployment device and wherein the therapy manager component is configured to prepare to deliver the therapy at least in part by directing the at least one gel deployment device to deploy gel.

26. The ambulatory medical device of claim 20, wherein the at least two buttons are on opposite sides of a housing of the ambulatory medical device.

27. The ambulatory medical device of claim 20, wherein the at least two buttons are located adjacent each other on a housing of the ambulatory medical device.

28. The ambulatory medical device of claim 20, wherein the at least one processor is further configured to cause a speaker of the ambulatory medical device to communicate an audible alert to bystanders to not touch the patient prior to transmitting a defibrillating pulse of energy.

* * * * *

UNITED STATES PATENT AND TRADEMARK OFFICE
CERTIFICATE OF CORRECTION

PATENT NO.         : 10,806,940 B2
APPLICATION NO.    : 15/970125
DATED              : October 20, 2020
INVENTOR(S)        : Thomas E. Kaib et al.

Page 1 of 1

It is certified that error appears in the above-identified patent and that said Letters Patent is hereby corrected as shown below:

In the Specification

Column 2, Line 42, delete "of the".
Column 24, Line 2, delete "FIG. SA" and insert -- FIG. 5A --.

In the Claims

Column 27, Line 12, claim number 4, delete "ef".
Column 27, Line 48, claim number 11, delete "response buttons".

Signed and Sealed this
Twenty-fourth Day of November, 2020

Andrei Iancu
*Director of the United States Patent and Trademark Office*